US006790829B1

(12) United States Patent
Kelly et al.

(10) Patent No.: US 6,790,829 B1

(45) Date of Patent: Sep. 14, 2004

(54) CYCLIC DECAPEPTIDE ANTIBIOTICS

(75) Inventors: Michael T. Kelly, Blaine, WA (US); Raymond J. Andersen, Vancouver (CA); Jeff Gerard, Montréal (CA)

(73) Assignees: SeaTek Marine Biotechnology, Inc., Surrey (CA); University of British Columbia, Vancouver (CA)

(*) Notice: Subject to any disclaimer, the term of this patent is extended or adjusted under 35 U.S.C. 154(b) by 0 days.

(21) Appl. No.: 09/043,813

(22) PCT Filed: Jul. 25, 1997

(86) PCT No.: PCT/CA97/00529

§ 371 (c)(1), (2), (4) Date: Sep. 29, 1998

(87) PCT Pub. No.: WO98/04584

PCT Pub. Date: Feb. 5, 1998

(51) Int. Cl.$^7$ .......................... A61K 38/12; C07K 5/12

(52) U.S. Cl. .......................... 514/11; 514/15; 530/317; 530/328

(58) Field of Search .................... 514/11, 15; 530/317, 530/323, 328

(56) References Cited

U.S. PATENT DOCUMENTS

| | | | | |
|---|---|---|---|---|
| 4,874,850 A | * 10/1989 | Paradies | 536/3 |
| 5,545,618 A | * 8/1996 | Buckley et al. | 514/12 |
| 6,323,312 B1 | 11/2001 | Rivier | 530/306 |
| 6,358,921 B1 | 3/2002 | Kondejewski et al. | 514/11 |
| 6,372,474 B1 | 4/2002 | Ueda et al. | 435/231 |
| 6,511,961 B1 | 1/2003 | Takahashi et al. | 514/9 |
| 6,511,962 B1 | 1/2003 | Borders et al. | 514/11 |
| 6,514,727 B1 | 2/2003 | Selsted et al. | 435/69.3 |
| 6,551,994 B1 | 4/2003 | Blaschuk et al. | 514/11 |

OTHER PUBLICATIONS

Gerrard et al., "Loloatin B, A cyclic Decapeptide Antibiotic Produced in Culture by a Tropical Marine Bacterium" Tetra. Letters. vol. 37, No. 40. pp. 7201–7204, 1996.*

Dayhoff, M. 'Atlas of Protein Sequence and Structure 1972', Wash. D.C.:National Biomedical Research Foundation, vol. 5, p. 76, 1972.*

Budavari et al. (eds.), *The Merck Index*, 11$^{th}$ ed., Merck & Co., Inc., Rahway, N.J., 1989, p. 712, compound No. 4438.

Budavari et al. (eds.), *The Merck Index*, 11$^{th}$ ed., Merck & Co., Inc., Rahway, N.J., 1989, p. 712, compound No. 4439.

Edmond et al., "Vancomycin–Resistant *Enterococcus faecium* Bacteremia: Risk Factors for Infectious," *Clinical Infection Diseases 20*: 1126–33, 1995.

Gerard et al., "Loloatin B, A Cyclic Decapeptide Antibiotic Produced in Culture by a Tropical Marine Bacterium," *Tetrahedron Letters 37*(40): 7201–7204, 1996.

Hotchkiss, "Gramicidin, Tyrocidine, and Tyrothricin," *Advances in Enzymology and Related Subjects 4*: 153–199, 1944.

Kosui et al., "Studies of Peptide Antibiotics. XLI. Syntheses of 6–L–Valine–Tyrocidine A and 7–L–Ornithine–Tyrocidine A," *Int. J. Peptide Protein Res. 18*: 127–134, 1981.

Ohno and Izumiya, "Synthesis of Tyrocidine A," *Journal of the American Chemical Society 88*(2): 376–378, 1966.

Okamoto et al., "Studies of Peptide Antibiotics. XXXIV. Syntheses of Tyrocidine A and Its Analogs Containing Glycine," *Bulletin of the Chemical Society of Japan 50*(1): 231–236, 1977.

* cited by examiner

*Primary Examiner*—Brenda Brumback
*Assistant Examiner*—Anish Gupta
(74) *Attorney, Agent, or Firm*—Seed IP Law Group PLLC

(57) ABSTRACT

Several cyclic decapeptides having antibiotic activity are disclosed. The decapeptides are active against both gram positive and gram negative bacteria.

6 Claims, No Drawings

SEQUENCE LISTING

```
<160> NUMBER OF SEQ ID NOS: 78

<210> SEQ ID NO 1
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
```

-continued

```
<222> LOCATION: (4)...(4)
<223> OTHER INFORMATION: Residue is D-Tyrosine
<220> FEATURE:
<221> NAME/KEY: VARIANT
<222> LOCATION: (7)...(7)
<223> OTHER INFORMATION: Residue is D-Phenylalanine

<400> SEQUENCE: 1

Val Xaa Leu Tyr Pro Phe Phe Asn Asp Tyr
 1              5                   10


<210> SEQ ID NO 2
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (4)...(4)
<223> OTHER INFORMATION: Residue is D-Tyrosine
<220> FEATURE:
<221> NAME/KEY: VARIANT
<222> LOCATION: (7)...(7)
<223> OTHER INFORMATION: Residue D-Phenylalanine

<400> SEQUENCE: 2

Val Xaa Leu Tyr Pro Phe Phe Asn Asp Trp
 1              5                   10


<210> SEQ ID NO 3
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (4)...(4)
<223> OTHER INFORMATION: Residue is D-Tyrosine
<220> FEATURE:
<221> NAME/KEY: VARIANT
<222> LOCATION: (7)...(7)
<223> OTHER INFORMATION: Residue is D-Phenylalanine

<400> SEQUENCE: 3

Val Xaa Leu Tyr Pro Trp Phe Asn Asp Trp
 1              5                   10


<210> SEQ ID NO 4
<211> LENGTH: 10
<212> TYPE: PRT
<213> ORGANISM: Bacillus laterosporus
<220> FEATURE:
<221> NAME/KEY: MOD_RES
<222> LOCATION: (1)...(1)
<223> OTHER INFORMATION: Butyrine
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry
```

-continued

<400> SEQUENCE: 4

```
Xaa Xaa Leu Tyr Pro Phe Phe Asn Asp Tyr
 1               5                   10
```

<210> SEQ ID NO 5
<211> LENGTH: 10
<212> TYPE: PRT
<213> ORGANISM: Bacillus laterosporus
<220> FEATURE:
<221> NAME/KEY: MOD_RES
<222> LOCATION: (1)...(1)
<223> OTHER INFORMATION: Butyrine
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 5

```
Xaa Xaa Leu Tyr Pro Phe Phe Asn Asp Trp
 1               5                   10
```

<210> SEQ ID NO 6
<211> LENGTH: 10
<212> TYPE: PRT
<213> ORGANISM: Bacillus laterosporus
<220> FEATURE:
<221> NAME/KEY: MOD_RES
<222> LOCATION: (1)...(1)
<223> OTHER INFORMATION: Butyrine
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 6

```
Xaa Xaa Leu Tyr Pro Trp Phe Asn Asp Trp
 1               5                   10
```

<210> SEQ ID NO 7
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Dbu
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 7

```
Val Xaa Leu Tyr Pro Phe Phe Asn Asp Tyr
 1               5                   10
```

-continued

<210> SEQ ID NO 8
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Dbu
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 8

Val Xaa Leu Tyr Pro Phe Phe Asn Asp Trp
1 5 10

<210> SEQ ID NO 9
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Dbu
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 9

Val Xaa Leu Tyr Pro Trp Phe Asn Asp Trp
1 5 10

<210> SEQ ID NO 10
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 10

Val Xaa Ile Tyr Pro Phe Phe Asn Asp Tyr
1 5 10

<210> SEQ ID NO 11
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.

-continued

In preferred embodiment residues 1-3, 5-6, 8-10 have
L-stereochemistry and residues 4 and 7 have
D-stereochemistry

<400> SEQUENCE: 11

Val Xaa Ile Tyr Pro Phe Phe Asn Asp Trp
1 5 10

<210> SEQ ID NO 12
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 12

Val Xaa Ile Tyr Pro Trp Phe Asn Asp Trp
1 5 10

<210> SEQ ID NO 13
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: aIle
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 13

Val Xaa Xaa Tyr Pro Phe Phe Asn Asp Tyr
1 5 10

<210> SEQ ID NO 14
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: aIle
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 14

-continued

```
Val Xaa Xaa Tyr Pro Phe Phe Asn Asp Trp
 1               5                  10


<210> SEQ ID NO 15
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: aIle
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 15

Val Xaa Xaa Tyr Pro Trp Phe Asn Asp Trp
 1               5                  10


<210> SEQ ID NO 16
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: Nva
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 16

Val Xaa Xaa Tyr Pro Phe Phe Asn Asp Tyr
 1               5                  10


<210> SEQ ID NO 17
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: Nva
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 17
```

-continued

```
Val Xaa Xaa Tyr Pro Phe Phe Asn Asp Trp
 1              5                  10


<210> SEQ ID NO 18
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: Nva
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 18

Val Xaa Xaa Tyr Pro Trp Phe Asn Asp Trp
 1              5                  10


<210> SEQ ID NO 19
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: Cyclopropylalanine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 19

Val Xaa Xaa Tyr Pro Phe Phe Asn Asp Tyr
 1              5                  10


<210> SEQ ID NO 20
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: Cyclopropylalanine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 20

Val Xaa Xaa Tyr Pro Phe Phe Asn Asp Trp
```

-continued

```
 1               5                  10


<210> SEQ ID NO 21
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: Cyclopropylalanine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 21

Val Xaa Xaa Tyr Pro Trp Phe Asn Asp Trp
 1               5                  10


<210> SEQ ID NO 22
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: Nle
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 22

Val Xaa Xaa Tyr Pro Phe Phe Asn Asp Tyr
 1               5                  10


<210> SEQ ID NO 23
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: Nle
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 23

Val Xaa Xaa Tyr Pro Phe Phe Asn Asp Trp
 1               5                  10
```

-continued

```
<210> SEQ ID NO 24
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (3)...(3)
<223> OTHER INFORMATION: Nle
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 24

Val Xaa Xaa Tyr Pro Trp Phe Asn Asp Trp
 1               5                  10


<210> SEQ ID NO 25
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (4)...(4)
<223> OTHER INFORMATION: p-fluorophenylalmine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 25

Val Xaa Leu Xaa Pro Phe Phe Asn Asp Tyr
 1               5                  10


<210> SEQ ID NO 26
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (4)...(4)
<223> OTHER INFORMATION: p-fluorophenylalmine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 26

Val Xaa Leu Xaa Pro Phe Phe Asn Asp Trp
 1               5                  10
```

-continued

<210> SEQ ID NO 27
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (4)...(4)
<223> OTHER INFORMATION: p-fluorophenylalmine
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 27

Val Xaa Leu Xaa Pro Trp Phe Asn Asp Trp
1 5 10

<210> SEQ ID NO 28
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 28

Val Xaa Leu Trp Pro Phe Phe Asn Asp Tyr
1 5 10

<210> SEQ ID NO 29
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 29

Val Xaa Leu Trp Pro Phe Phe Asn Asp Trp
1 5 10

<210> SEQ ID NO 30
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn -continued

```
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 30

Val Xaa Leu Trp Pro Trp Phe Asn Asp Trp
 1               5                  10


<210> SEQ ID NO 31
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (4)...(4)
<223> OTHER INFORMATION: Thienylalanine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 31

Val Xaa Leu Xaa Pro Phe Phe Asn Asp Tyr
 1               5                  10


<210> SEQ ID NO 32
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (4)...(4)
<223> OTHER INFORMATION: Thienylalanine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 32

Val Xaa Leu Xaa Pro Phe Phe Asn Asp Trp
 1               5                  10


<210> SEQ ID NO 33
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (4)...(4)
<223> OTHER INFORMATION: Thienylalanine
<220> FEATURE:
```

-continued

```
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 33

Val Xaa Leu Xaa Pro Trp Phe Asn Asp Trp
 1               5                   10


<210> SEQ ID NO 34
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: Azetidine-2-carboxylic acid
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 34

Val Xaa Leu Tyr Xaa Phe Phe Asn Asp Tyr
 1               5                   10


<210> SEQ ID NO 35
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: Azetidine-2-carboxylic acid
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 35

Val Xaa Leu Tyr Xaa Phe Phe Asn Asp Trp
 1               5                   10


<210> SEQ ID NO 36
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: Azetidine-2-carboxylic acid
<220> FEATURE:
<221> NAME/KEY: VARIANT
```

-continued

```
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 36

Val Xaa Leu Tyr Xaa Trp Phe Asn Asp Trp
 1               5                  10


<210> SEQ ID NO 37
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: Pipecolic acid
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 37

Val Xaa Leu Tyr Xaa Phe Phe Asn Asp Tyr
 1               5                  10


<210> SEQ ID NO 38
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: Pipecolic acid
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 38

Val Xaa Leu Tyr Xaa Phe Phe Asn Asp Trp
 1               5                  10


<210> SEQ ID NO 39
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: Pipecolic acid
<220> FEATURE:
<221> NAME/KEY: VARIANT
<222> LOCATION: (1)...(10)
```

-continued

<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 39

Val Xaa Leu Tyr Xaa Trp Phe Asn Asp Trp
 1               5                   10

<210> SEQ ID NO 40
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: trans-3-methylproline
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 40

Val Xaa Leu Tyr Xaa Phe Phe Asn Asp Tyr
 1               5                   10

<210> SEQ ID NO 41
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: trans-3-methylproline
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 41

Val Xaa Leu Tyr Xaa Phe Phe Asn Asp Trp
 1               5                   10

<210> SEQ ID NO 42
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: trans-3-methylproline
<220> FEATURE:
<221> NAME/KEY: VARIANT
<222> LOCATION: (1)...(10)
<223> OTHER INFORMATION: All residues can have L- or D- Stereochemistry.

-continued

In preferred embodiment residues 1-3, 5-6, 8-10 have
L-stereochemistry and residues 4 and 7 have
D-stereochemistry

<400> SEQUENCE: 42

Val Xaa Leu Tyr Xaa Trp Phe Asn Asp Trp
1 5 10

<210> SEQ ID NO 43
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: trans-4-fluoroproline
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 43

Val Xaa Leu Tyr Xaa Phe Phe Asn Asp Tyr
1 5 10

<210> SEQ ID NO 44
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: trans-4-fluoroproline
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 44

Val Xaa Leu Tyr Xaa Phe Phe Asn Asp Trp
1 5 10

<210> SEQ ID NO 45
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: trans-4-fluoroproline
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have -continued

```
      L-stereochemistry and residues 4 and 7 have
      D-stereochemistry

<400> SEQUENCE: 45

Val Xaa Leu Tyr Xaa Trp Phe Asn Asp Trp
 1               5                  10


<210> SEQ ID NO 46
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 46

Val Xaa Leu Tyr Pro Tyr Phe Asn Asp Tyr
 1               5                  10


<210> SEQ ID NO 47
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 47

Val Xaa Leu Tyr Pro Tyr Phe Asn Asp Trp
 1               5                  10


<210> SEQ ID NO 48
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (6)...(6)
<223> OTHER INFORMATION: p-fluorophenylalamine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 48

Val Xaa Leu Tyr Pro Xaa Phe Asn Asp Tyr
 1               5                  10
```

-continued

```
<210> SEQ ID NO 49
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (6)...(6)
<223> OTHER INFORMATION: p-fluorophenylalamine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 49

Val Xaa Leu Tyr Pro Xaa Phe Asn Asp Trp
 1               5                  10


<210> SEQ ID NO 50
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 50

Val Xaa Leu Tyr Pro Trp Phe Asn Asp Tyr
 1               5                  10


<210> SEQ ID NO 51
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 51

Val Xaa Leu Tyr Pro Trp Phe Asn Asp Trp
 1               5                  10


<210> SEQ ID NO 52
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
```

-continued

<221> NAME/KEY: MOD_RES
<222> LOCATION: (6)...(6)
<223> OTHER INFORMATION: Thienylalanine
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 52

```
Val Xaa Lys Tyr Pro Xaa Phe Asn Asp Tyr
 1               5                  10
```

<210> SEQ ID NO 53
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (6)...(6)
<223> OTHER INFORMATION: Thienylalanine
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 53

```
Val Xaa Leu Tyr Pro Xaa Phe Asn Asp Trp
 1               5                  10
```

<210> SEQ ID NO 54
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (6)...(6)
<223> OTHER INFORMATION: beta-phenylserine
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 54

```
Val Xaa Leu Tyr Pro Xaa Phe Asn Asp Tyr
 1               5                  10
```

<210> SEQ ID NO 55
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES -continued

```
<222> LOCATION: (6)...(6)
<223> OTHER INFORMATION: beta-phenylserine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 55

Val Xaa Leu Tyr Pro Xaa Phe Asn Asp Trp
 1               5                  10


<210> SEQ ID NO 56
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 56

Val Xaa Leu Tyr Pro Phe Tyr Asn Asp Tyr
 1               5                  10


<210> SEQ ID NO 57
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 57

Val Xaa Leu Tyr Pro Phe Tyr Asn Asp Trp
 1               5                  10


<210> SEQ ID NO 58
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (7)...(7)
<223> OTHER INFORMATION: p-fluorophenylalamine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry
```

-continued

<400> SEQUENCE: 58

Val Xaa Leu Tyr Pro Phe Xaa Asn Asp Tyr
1 5 10

<210> SEQ ID NO 59
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (7)...(7)
<223> OTHER INFORMATION: p-fluorophenylalamine
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 59

Val Xaa Leu Tyr Pro Phe Xaa Asn Asp Trp
1 5 10

<210> SEQ ID NO 60
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 60

Val Xaa Leu Tyr Pro Phe Trp Asn Asp Tyr
1 5 10

<210> SEQ ID NO 61
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 61

Val Xaa Leu Tyr Pro Phe Trp Asn Asp Trp
1 5 10

<210> SEQ ID NO 62
<211> LENGTH: 10

-continued

```
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (7)...(7)
<223> OTHER INFORMATION: Thienylalanine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 62

Val Xaa Leu Tyr Pro Phe Xaa Asn Asp Tyr
 1               5                  10


<210> SEQ ID NO 63
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (7)...(7)
<223> OTHER INFORMATION: Thienylalanine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 63

Val Xaa Leu Tyr Pro Phe Xaa Asn Asp Trp
 1               5                  10


<210> SEQ ID NO 64
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (7)...(7)
<223> OTHER INFORMATION: beta-phenylserine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 64

Val Xaa Leu Tyr Pro Phe Xaa Asn Asp Tyr
 1               5                  10


<210> SEQ ID NO 65
<211> LENGTH: 10
<212> TYPE: PRT
```

-continued

<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (7)...(7)
<223> OTHER INFORMATION: beta-phenylserine
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 65

Val Xaa Leu Tyr Pro Phe Xaa Asn Asp Trp
1 5 10

<210> SEQ ID NO 66
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 66

Val Xaa Leu Tyr Pro Trp Phe Asn Asp Tyr
1 5 10

<210> SEQ ID NO 67
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (10)...(10)
<223> OTHER INFORMATION: p-fluorophenylalamine
<220> FEATURE:
<221> NAME/KEY: VARIANT
<222> LOCATION: (1)...(10)
<223> OTHER INFORMATION: All residues can have L- or D- Stereochemistry.
In preferred embodiment residues 1-3, 5-6, 8-10 have
L-stereochemistry and residues 4 and 7 have
D-stereochemistry

<400> SEQUENCE: 67

Val Xaa Leu Tyr Pro Phe Phe Asn Asp Xaa
1 5 10

<210> SEQ ID NO 68
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn -continued
<220> FEATURE:
<221> NAME/KEY: MOD_RES
<222> LOCATION: (10)...(10)
<223> OTHER INFORMATION: p-fluorophenylalamine
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 68

Val Xaa Leu Tyr Pro Trp Phe Asn Asp Xaa
1 5 10

<210> SEQ ID NO 69
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 69

Val Xaa Leu Tyr Pro Phe Phe Asn Asp Phe
1 5 10

<210> SEQ ID NO 70
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have L-stereochemistry and residues 4 and 7 have D-stereochemistry

<400> SEQUENCE: 70

Val Xaa Leu Tyr Pro Trp Phe Asn Asp Phe
1 5 10

<210> SEQ ID NO 71
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (10)...(10)
<223> OTHER INFORMATION: Thienylalanine
<220> FEATURE:
<221> NAME/KEY: VARIANT
<222> LOCATION: (1)...(10)
<223> OTHER INFORMATION: All residues can have L- or D- Stereochemistry. In preferred embodiment residues 1-3, 5-6, 8-10 have -continued

```
      L-stereochemistry and residues 4 and 7 have
      D-stereochemistry

<400> SEQUENCE: 71

Val Xaa Leu Tyr Pro Phe Phe Asn Asp Xaa
 1               5                  10


<210> SEQ ID NO 72
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (10)...(10)
<223> OTHER INFORMATION: Thienylalanine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 72

Val Xaa Leu Tyr Pro Trp Phe Asn Asp Xaa
 1               5                  10


<210> SEQ ID NO 73
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (10)...(10)
<223> OTHER INFORMATION: beta-phenylserine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
      D-stereochemistry

<400> SEQUENCE: 73

Val Xaa Leu Tyr Pro Phe Phe Asn Asp Xaa
 1               5                  10


<210> SEQ ID NO 74
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (10)...(10)
<223> OTHER INFORMATION: beta-phenylserine
<220> FEATURE:
<221> NAME/KEY: VARIANT
<222> LOCATION: (1)...(10)
<223> OTHER INFORMATION: All residues can have L- or D- Stereochemistry.
      In preferred embodiment residues 1-3, 5-6, 8-10 have
      L-stereochemistry and residues 4 and 7 have
```

-continued

D-stereochemistry

<400> SEQUENCE: 74

Val Xaa Leu Tyr Pro Trp Phe Asn Asp Xaa
1 5 10

<210> SEQ ID NO 75
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry

<400> SEQUENCE: 75

Val Xaa Leu Tyr Pro Phe Phe Asn Asp Tyr
1 5 10

<210> SEQ ID NO 76
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry

<400> SEQUENCE: 76

Val Xaa Leu Tyr Pro Phe Phe Asn Asp Trp
1 5 10

<210> SEQ ID NO 77
<211> LENGTH: 10
<212> TYPE: PRT
<213> ORGANISM: Bacillus laterosporus
<220> FEATURE:
<221> NAME/KEY: MOD_RES
<222> LOCATION: (2)...(2)
<223> OTHER INFORMATION: Orn
<220> FEATURE:
<221> NAME/KEY: VARIANT
<222> LOCATION: (1)...(10)
<223> OTHER INFORMATION: All residues can have L- or D- Stereochemistry

<400> SEQUENCE: 77

Val Xaa Leu Tyr Pro Trp Phe Asn Asp Trp
1 5 10

<210> SEQ ID NO 78
<211> LENGTH: 5
<212> TYPE: PRT
<213> ORGANISM: Bacillus laterosporus
<220> FEATURE:
<221> NAME/KEY: MOD_RES
<222> LOCATION: (3)...(3)
<223> OTHER INFORMATION: Orn

<400> SEQUENCE: 78

Trp Val Xaa Leu Tyr
1 5

CYCLIC DECAPEPTIDE ANTIBIOTICS

TECHNICAL FIELD

The present invention relates to novel cyclic peptide compounds with potent activity against antibiotic-resistant pathogens.

BACKGROUND OF THE INVENTION

Methicillin-resistant strains of *Staphylococcus aureus* (USA) cause infections that are refractory to standard anti-staphylococci antibiotics, and in many cases vancomycin is the antibiotic of last resort. Consequently, it is of great concern that vancomycin-resistant strains of MRSA may develop.

Infections due to enterococci have been difficult to treat for many years because these organisms are intrinsically resistant to many antibiotics. Ampicillin has been the mainstay for treatment of uncomplicated enterococcal infections, but many strains have now become resistant to ampicillin. Vancomycin is again the only effective treatment for these ampicillin-resistant enterococcal infections. In the past few years, vancomycin-resistant enterococcal strains (VRE) have begun to appear and they are rapidly spreading across North America. There are no effective antibiotics currently available for such organisms and the recent report of an outbreak of VRE with a 73% mortality rate has highlighted the seriousness of the situation. See Edmond, M. B. et al., *Clinical Infectious Diseases* 20:1126–33, 1995.

One area where new drugs are desperately needed is in the treatment of antibiotic-resistant strains of gram positive human pathogens. The present invention is directed to fulfilling this need, and provides related advantages as described herein.

SUMMARY OF THE INVENTION

In a first aspect, the invention is directed to isolated cyclic decapeptides of the formulas (1), (2) and (3):

(1): cyclo [L-Val-L-Orn-L-Leu-D-Tyr-L-Pro-L-Phe-D-Phe-L-Asn-Asp-L-Tyr] (SEQ ID NO:1);

(2): cyclo [L-Val-L-Orn-L-Leu-D-Tyr-L-Pro-L-Phe-D-Phe-L-Asn-L-Asp-L-Trp] (SEQ ID NO:2); and (3) cyclo [L-Val-L-Orn-L-Leu-D-Tyr-L-Pro-L-Trp-D-Phe-L-Asn-L-Asp-L-Trp] (SEQ ID NO:3).

The decapeptide of Formula (1) is referred to herein as Loloatin A. The decapeptide of Formula (2) is referred to herein as Loloatin B. The decapeptide of Formula (3) is referred to herein as Loloatin C.

The invention is directed to the above-identified cyclic decapeptides in an isolated, i.e., substantially purified form, preferably in a quantity of more than about 1 gram, more preferably in a quantity of more than about 10 grams, still more preferably in a quantity of more than about 100 grams, and yet still more preferably in a quantity of more than about 1 kilogram. A substantially purified form is a composition wherein the above-listed cyclic decapeptides constitute at least about 1 weight percent of the composition, preferably at least about 10 weight percent, more preferably at least about 30 weight percent, still more preferably at least about 50 weight percent, yet still more preferably at least about 70 weight percent, and yet still more preferably at least about 95 weight percent, and most preferably at least about 99 weight percent.

The invention is also directed to the above-identified cyclic decapeptides in a pharmaceutical composition. A pharmaceutical composition of the invention may not necessarily contain the cyclic decapeptide in a substantially purified form because the composition may contain diluent and/or other materials commonly found in pharmaceutical compositions.

The invention is also directed to a method of treating bacterial infection, comprising administering to a patient having a bacterial infection, an amount of the above-identified cyclic decapeptides effective to relieve symptoms associated with or due to the bacterial infection.

In another aspect, the invention is directed to various derivatives and analogs of Loloatin A, B and C.

Loloatin derivatives of the invention include the solvates, salts (either acid- or base- addition salts, depending on whether the amino acid sidechain being converted to a salt is basic or acidic, respectively), esters (derivatives of amino acid sidechains containing a carboxylic acid group), amines (derivatives of amino acid sidechains containing an amino group), ethers (derivatives of amino acid sidechains containing an hydroxyl group) and amides (derivatives of amino acid sidechains containing either an amine or carboxylic acid group) of Loloatin A, B or C.

For example, the invention provides for a salt of a compound selected from the group:

cyclo[L-Val-L-Orn-L-Leu-D-Tyr-L-Pro-L-Phe-D-Phe-L-Asn-L-Asp-L-Tyr] (SEQ ID NO:1);

cyclo[L-Val-L-Orn-L-Leu-D-Tyr-L-Pro-L-Phe-D-Phe-L-Asn-L-Asp-L-Trp] (SEQ ID NO:2); and cyclo[L-Val-L-Orn-L-Leu-D-Tyr-L-Pro-L-Trp-D-Phe-L-Asn-L-Asp-L-Trp] (SEQ ID NO:3).

The salt may contain at least one negatively charged ion selected from chloride, bromide, sulfate, phosphate, $C_{1-15}$carboxylate, methanesulfonate and p-toluenesulfonate, which are exemplary only. Exemplary $C_{1-15}$carboxylates include acetate, glycolate, lactate, pyruvate, malonate, succinate, glutarate, fumarate, malate, tartarate, citrate, ascorbate, maleate, hydroxymaleate, benzoate, hydroxybenzoate, phenylacetate, cinnamate, salicylate and 2-phenoxybenzoate.

The salt may contain at least one positively charged ion selected from lithium, sodium, potassium, beryllium, magnesium, calcium and quaternary ammonium ions, which are exemplary positively charged ions. Exemplary quaternary ammonium ions cinlude tetraallylammonium, and trialkylaralkylammonium ions.

The invention also provides for derivatives of a compound selected from cyclo[L-Val-L-Orn-L-Leu-D-Tyr-L-Pro-L-Phe-D-Phe-L-Asn-L-Asp-L-Tyr] (SEQ ID NO:1);

cyclo[L-Val-L-Orn-L-Leu-D-Tyr-L-Pro-L-Phe-D-Phe-L-Asn-L-Asp-L-Trp] (SEQ ID NO:2); and cyclo[L-Val-L-Orn-L-Leu-D-Tyr-L-Pro-L-Trp-D-Phe-L-Asn-L-Asp-L-Trp] (SEQ ID NO:3).

For example, the derivative may have the amine group of the ornithine sidechain being a secondary, tertiary or quaternary amine group, and other amino acid sidechains are optionally in a derivative form as well. Exemplary ornithine sidechains have the formula $—CH_2—CH_2—CH_2—NHR^3$, $—CH_2—CH_2—CH_2—N(R^3)_2$ or $—CH_2—CH_2—CH_2—N(R^3)_3$ wherein $R^3$ is an alkyl group that may be of straight chain, or where possible, of cyclic or branched structure and may contain one or more alkene, alkyne, or aromatic functionalities; or an acyl group that may be of straight chain, or where possible, of cyclic or branched structure and may contain one or more alkene, alkyne, or aromatic functionalities.

In other derivatives, the hydroxyl group of one or more tyrosine sidechains has been converted to an ether or ester group, and other amino acid sidechains are optionally in a derivative form as well. For example, at least one tyrosine sidechain may have the formula —$CH_2$—$C_6H_4$—O—$R^2$, wherein $C_6H_4$ is an aromatic ring and —O—$R^2$ is in the para position, and $R^2$ is a $C_{1-15}$ alkyl group so as to form an ether, where the alkyl group may be of straight chain, or where possible, of cyclic or branched structure and may contain one or more alkene, alkyne, or aromatic functionalities; or a $C_{1-15}$ acyl group so as to form an ester, where the acyl group may be of straight chain, or where possible, of cyclic or branched structure and may contain one or more alkene, alkyne, or aromatic functionalities.

In other derivatives, the carboxyl group of the aspartic acid sidechain has been converted to an amide or ester group, and other amino acid sidechains are optionally in a derivative form as well. For example, the aspartic acid sidechain may have the formula —$CH_2$—C(═O)O—$R^1$, and $R^1$ is a $C_{1-15}$ alkyl group that may be of straight chain, or where possible, of cyclic or branched structure and may contain one or more alkene, alkyne, or aromatic functionalities; or an aryl group. In another example, the aspartic acid sidechain has the formula —$CH_2$—C(═O)N—$R^1$, and $R^1$ is a $C_{1-15}$ alkyl group that may be of straight chain, or where possible, of cyclic or branched structure and may contain one or more alkene, alkyne, or aromatic functionalities; or an aryl group.

The invention also provides for a pharmaceutical composition comprising a salt, derivative or analog of any of Loloatin A, Loloatin B and Loloatin C, as set forth above, in admixture with a pharmaceutically acceptable carrier.

The invention also provides for a method for the treatment of a patient afflicted with a bacterial infection comprising the administration to said patient of a therapeutically effective amount of a salt, derivative or analog of any of Loloatin A, Loloatin B and Loloatin C, as set forth above The invention also provides for the use of a salt, derivative or analog of any of Loloatin A, Loloatin B and Loloatin C, as set forth above, in the manufacture of a medicament, where the medicament may be used to treat bacterial infection.

The Loloatin analogs include cyclic decapeptides having a "non-natural" stereochemistry at one or more of the α-carbons of the component amino acids, where the "natural" stereochemistry is as indicated by the L- or D- designations preceding the name of each of the amino acids in the formulas for Loloatin A, B and C set forth above. Collectively, these Loloatin analogs are represented by the formulae:

cyclo[Val-Orn-Leu-Tyr-Pro-Phe-Phe-Asn-Asp-Try] (SEQ ID NO:75);

cyclo[Val-Orn-Leu-Tyr-Pro-Phe-Phe-Asn-Asp-Trp] (SEQ ID NO:76); and cyclo[Val-Orn-Leu-Tyr-Pro-Trp-Phe-Asn-Asp-Trp] (SEQ ID NO:77).

Furthermore, the invention is directed to various analogs of the above-identified compounds, where preferred analogs have the formulas listed below. In the below-listed structures, no stereochemistry is designated because the analogs of the invention may have any possible stereochemistry at each atom capable of having more than one stereochemical arrangement of substituents. However, looking at the below listed sequences from left to right as written, preferred analogs have the stereochemistry L-, L-, L-, D-, L-, L-, D-, L-, L- and L-. For example, cyclo[Val-Orn-Leu-Tyr-Pro-Trp-Phe-Asn-Asp-β-Phenylserine] (SEQ ID NO:74), as written below preferably has the stereochemistry cyclo[L-Val-L-Orn-L-Leu-D-Tyr-L-Pro-L-Trp-D-Phe-L-Asn-L-Asp-L-β-Phenylserine] (SEQ ID NO:74).

Preferred analogs have one amino acid residue present in Loloatin A, B or C replaced with a different amino acid residue. Preferred analogs are:

cyclo[Butyrine-Orn-Leu-Tyr-Pro-Phe-Phe-Asn-Asp-Tyr] (SEQ ID NO:4), cyclo[Butyrine-Orn-Leu-Tyr-Pro-Phe-Phe-Asn-Asp-Trp] (SEQ ID NO:5);

cyclo[Butyrine-Orn-Leu-Tyr-Pro-Trp-Phe-Asn-Asp-Trp] (SEQ ID NO:6);

cyclo[Val-diaminobutyric aicd-Leu-Tyr-Pro-Phe-Phe-Asn-Asp-Tyr] (SEQ ID NO:7);

cyclo[Val diaminobutyric aicd-Leu-Try-Pro-Phe-Phe-Asn-Asp-Trp] (SEQ ID NO:8);

cyclo[Val-diaminobutyric aicd-Leu-Tyr-Pro-Trp-Phe-Asn-Asp-Trp] (SEQ ID NO:9);

cyclo[Val-Orn-Isoleucine-Tyr-Pro-Phe-Phe-Asn-Asp-Tyr] (SEQ ID NO:10);

cyclo[Val-Orn-Isoleucine-Tyr-Pro-Phe-Phe-Asn-Asp-Trp] (SEQ ID NO:11);

cyclo[Val-Orn-Isoleucine-Tyr-Pro-Trp-Phe-Asn-Asp-Trp] (SEQ ID NO:12);

cyclo[Val-Orn-Alloisoleucine-Tyr-Pro-Phe-Phe-Asn-Asp-Tyr] (SEQ ID NO:13);

cyclo[Val-Orn-Alloisoleucine-Tyr-Pro-Phe-Phe-Asn-Asp-Tyr] (SEQ ID NO:14);

cyclo[Val-Orn-Alloisoleucine-Tyr-Pro-Trp-Phe-Asn-Asp-Trp] (SEQ ID NO:15);

cyclo[Val-Orn-Norvaline-Tyr-Pro-Phe-Phe-Asn-Asp-Tyr] (SEQ ID NO:16);

cyclo[Val-Orn-Norvaline-Tyr-Pro-Phe-Phe-Asn-Asp-Trp] (SEQ ID NO:17);

cyclo[Val-Orn-Norvaline-Tyr-Pro-Trp-Phe-Asn-Asp-Trp] (SEQ ID NO:18);

cyclo[Val-Orn-Cyclopropylalanine-Tyr-Pro-Phe-Phe-Asn-Asp-Tyr] (SEQ ID NO:19);

cyclo[Val-Orn-Cyclopropylalanine-Tyr-Pro-Phe-Phe-Asn-Asp-Trp] (SEQ ID NO:20);

cyclo[Val-Orn-Cyclopropylalanine-Tyr-Pro-Trp-Phe-Asn-Asp-Trp] (SEQ ID NO:21);

cyclo[Val-Orn-Norleucine-Tyr-Pro-Phe-Phe-Asn-Asp-Tyr] (SEQ ID NO:22);

cyclo[Val-Orn-Norleucine-Try-Pro-Phe-Phe-Asn-Asp-Trp] (SEQ ID NO:23);

cyclo[Val-Orn-Norleucine-Tyr-Pro-Trp-Phe-Asn-Asp-Trp] (SEQ ID NO:24);

cyclo[Val-Orn-Norleucine-Tyr-Pro-Phe-Phe-Asn-Asp-Tyr] (SEQ ID NO:22);

cyclo[Val-Orn-Norleucine-Tyr-Pro-Phe-Phe-Asn-Asp-Trp] (SEQ ID NO:23);

cyclo[Val-Orn-Norleucine-Tyr-Pro-Trp-Phe-Asn-Asp-Trp] (SEQ ID NO:24);

cyclo[Val-Orn-Leu-p-fluorophenylalamine-Pro-Phe-Phe-Asn-Asp-Tyr] (SEQ ID NO:25);

cyclo[Val-Orn-Leu-p-fluorophenylalamine-Pro-Phe-Phe-Asn-Asp-Trp] (SEQ ID NO:26);

cyclo[Val-Orn-Leu-p-fluorophenylalamine-Pro-Trp-Phe-Asn-Asp-Trp] (SEQ ID NO:27);

cyclo[Val-Orn-Leu-Tryptophan-Pro-Phe-Phe-Asn-Asp-Tyr] (SEQ ID NO:28);

cyclo[Val-Orn-Leu-Tryptophan-Pro-Phe-Phe-Asn-Asp-Trp] (SEQ ID NO:29);

cyclo[Val-Orn-Leu-Tryptophan-Pro-Trp-Phe-Asn-Asp-Trp] (SEQ ID NO:30);

cyclo[Val-Orn-Leu-Thienylalanine-Pro-Phe-Phe-Asn-Asp-Tyr] (SEQ ID NO:31);

cyclo[Val-Orn-Leu-Thienylalanine-Pro-Phe-Phe-Asn-Asp-Trp] (SEQ ID NO:32);

cyclo[Val-Orn-Leu-Thienylalanine-Pro-Trp-Phe-Asn-Asp-Trp] (SEQ ID NO:33);

cyclo[Val-Orn-Leu-Tyr-Azetidine-2-carboxylic acid-Phe-Phe-Asn-Asp-Tyr] (SEQ ID NO:34);

cyclo[Val-Orn-Leu-Tyr-Azetidine-2-carboxylic acid-Phe-Phe-Asn-Asp-Trp] (SEQ ID NO:35);

cyclo[Val-Orn-Leu-Tyr-Azetidine-2-carboxylic acid-Trp-Phe-Asn-Asp-Trp] (SEQ ID NO:36);

cyclo[Val-Orn-Leu-Tyr-Pipecolic acid-Phe-Phe-Asn-Asp-Tyr] (SEQ ID NO:37);

cyclo[Val-Orn-Leu-Tyr-Pipecolic acid-Phe-Phe-Asn-Asp-Trp] (SEQ ID NO:38);

cyclo[Val-Orn-Leu-Tyr-Pipecolic acid-Trp-Phe-Asn-Asp-Trp] (SEQ ID NO:39);

cyclo[Val-Orn-Leu-Tyr-trans-3-Methylproline-Phe-Phe-Asn-Asp-Tyr] (SEQ ID NO:40);

cyclo[Val-Orn-Leu-Tyr-trans-3-Methylproline-Phe-Phe-Asn-Asp-Trp] (SEQ ID NO:41);

cyclo[Val-Orn-Leu-Tyr-trans-3-Methylproline-Trp-Phe-Asn-Asp-Trp] (SEQ ID NO:42);

cyclo[Val-Orn-Leu-Tyr-trans-4-Fluoroproline-Phe-Phe-Asn-Asp-Tyr] (SEQ ID NO:43);

cyclo[Val-Orn-Leu-Tyr-trans-4-Fluoroproline-Phe-Phe-Asn-Asp-Trp] (SEQ ID NO:44);

cyclo[Val-Orn-Leu-Tyr-trans-4-Fluoroproline-Trp-Phe-Asn-Asp-Trp] (SEQ ID NO:45);

cyclo[Val-Orn-Leu-Tyr-Pro-Tyr-Phe-Asn-Asp-Tyr] (SEQ ID NO:46);

cyclo[Val-Orn-Leu-Tyr-Pro-Tyr-Pher-Asn-Asp-Trp] (SEQ ID NO:47);

cyclo[Val-Orn-Leu-Tyr-Pro-p-Fluorophenylalanine-Phe-Asn-Asp-Tyr] (SEQ ID NO:48);

cyclo[Val-Orn-Leu-Tyr-Pro-p-Fluorophenylalanine-Phe-Asn-Asp-Trp] (SEQ ID NO:49);

cyclo[Val-Orn-Leu-Tyr-Pro-Trp-Phe-Asn-Asp-Tyr] (SEQ ID NO:50);

cyclo[Val-Orn-Leu-Tyr-Pro-Trp-Phe-Asn-Asp-Trp] (SEQ ID NO:51);

cyclo[Val-Orn-Leu-Tyr-Pro-Thienylalanine-Phe-Asn-Asp-Tyr] (SEQ ID NO:52)

cyclo[Val-Orn-Leu-Tyr-Pro-Thienylalanine-Phe-Asn-Asp-Trp] (SEQ ID NO:53)

cyclo[Val-Orn-Leu-Tyr-Pro-β-Phenylserine-Phe-Asn-Asp-Tyr] (SEQ ID NO:54);

cyclo[Val-Orn-Leu-Tyr-Pro-β-Phenylserine-Phe-Asn-Asp-Trp] (SEQ ID NO:55);

cyclo[Val-Orn-Leu-Tyr-Pro-Phe-Tyr-Asn-Asp-Tyr] (SEQ ID NO:56);

cyclo[Val-Orn-Leu-Tyr-Pro-Phe-Tyr-Asn-Asp-Trp] (SEQ ID NO:57);

cyclo[Val-Orn-Leu-Try-Phe-p-Fluorophenylalanine-Asn-Asp-Tyr] (SEQ ID NO:58);

cyclo[Val-Orn-Leu-Try-Phe-p-Fluorophenylalanine-Asn-Asp-Trp] (SEQ ID NO:59);

cyclo[Val-Orn-Leu-Tyr-Pro-Phe-Trp-Asn-Asp-Tyr] (SEQ ID NO:60);

cyclo[Val-Orn-Leu-Tyr-Pro-Phe-Trp-Asn-Asp-Trp] (SEQ ID NO:61);

cyclo[Val-Orn-Leu-Tyr-Pro-Phe-Thienylalanine-Asn-Asp-Tyr] (SEQ ID NO:62);

cyclo[Val-Orn-Leu-Tyr-Pro-Phe-Thienylalanine-Asn-Asp-Trp] (SEQ ID NO:63);

cyclo[Val-Orn-Leu-Try-Pro-Phe-β-Phenylserine-Asn-Asp-Tyr] (SEQ ID NO:64);

cyclo[Val-Orn-Leu-Try-Pro-Phe-β-Phenylserine-Asn-Asp-Trp] (SEQ ID NO:65);

cyclo[Val-Orn-Leu-Tyr-Pro-Trp-Phe-Asn-Asp-Tyr] (SEQ ID NO:66);

cyclo[Val-Orn-Leu-Tyr-Pro-Phe-Phe-Asn-Asp-p-Fluorophenylalanine] (SEQ ID NO:67);

cyclo[Val-Orn-Leu-Tyr-Pro-Trp-Phe-Asn-Asp-p-Fluorophenylalanine] (SEQ ID NO:68);

cyclo[Val-Orn-Leu-Tyr-Pro-Phe-Phe Asn-Asp-Phe] (SEQ ID NO:69);

cyclo[Val-Orn-Leu-Tyr-Pro-Trp-Phe-Asn-Asp-Phe] (SEQ ID NO:70);

cyclo[Val-Orn-Leu-Tyr-Pro-Phe-Phe-Asn-Asp-Thienylalanine] (SEQ ID NO:71);

cyclo[Val-Orn-Leu-Tyr-Pro-Trp-Phe-Asn-Asp-Thienylalanine] (SEQ ID NO:72);

cyclo[Val-Orn-Leu-Tyr-Pro-Phe-Phe-Asn-Asp-β-Phenylserine] (SEQ ID NO:73); and cyclo[Val-Orn-Leu-Tyr-Pro-Trp-Phe-Asn-Asp-β-Phenylserine] (SEQ ID NO:73).

The present invention is also directed to derivatives of the above-listed Loloatin analogs (i.e., analog derivatives), including the solvates, salts (either acid- or base- addition salts, depending on whether the amino acid sidechain being converted to a salt is basic or acidic, respectively), esters (derivatives of amino acid sidechains containing a carboxylic acid group), amine (derivatives of amino acid sidechains containing an amino group), ethers (derivatives of amino acid sidechains containing an hydroxyl group) and amides (derivatives of amino acid sidechains containing either an amine or carboxylic acid group) of the Loloatin A, B and C analogs listed above.

Collectively, the above-identified Loloatin A, B and C derivatives, analogs and analog derivatives are referred to herein as compounds of Formula (A), or compounds of the invention.

The invention is also directed to the compounds of the invention in an isolated, i.e., substantially purified form, preferably in a quantity of more than about 1 gram, more preferably in a quantity of more than about 10 grams, still more preferably in a quantity of more than about 100 grams, and yet still more preferably in a quantity of more than about 1 kilogram. A substantially purified form is a composition wherein the above-listed compound of the invention constitutes at least about 1 weight percent of the composition, preferably at least about 10 weight percent, more preferably at least about 30 weight percent, still more preferably at least about 50 weight percent, yet still more preferably at least about 70 weight percent, and yet still more preferably at least about 95 weight percent, and most preferably at least about 99 weight percent.

The invention is also directed to pharmaceutical compositions comprising compounds of the invention.

The invention is also directed to a method of treating bacterial infection, comprising administering to a patient having a bacterial infection, an amount of a compound of the invention effective to relieve symptoms associated with or due to the bacterial infection.

The compounds of the present invention contain multiple asymmetric carbon atoms and thus exist as enantiomers and diastereomers. Unless otherwise noted, the present invention includes all enantiomeric and diastereomeric forms of the compounds. Pure stereoisomers, mixtures of enantiomers and/or diastereomers, and mixtures of different compounds of the invention are included within the scope of the present invention.

The synthesis procedures described herein, especially when taken with the general knowledge in the art, provide sufficient guidance to those of ordinary skill in the art to perform the synthesis, isolation, and purification of the compounds described herein and other analogous compounds. Individual enantiomers may be obtained, if desired, from mixtures of the different forms by known methods of resolution, such as the formation of diastereomers, followed by recrystalisation. Alternatively, isomerically pure starting materials may be employed in the synthesis of a compound of the invention.

The compounds of the invention may be in the form of a solvate or a pharmaceutically acceptable salt, e.g., an acid- or base- addition salt. Such salts may have at least one negatively charged ion such as chloride, bromide, sulfate, phosphate, $C_{1-15}$carboxylate, methanesulfonate and p-toluenesulfonate, where exemplary $C_{1-15}$carboxylate ions are acetate, glycolate, lactate, pyruvate, malonate, succinate, glutarate, fumarate, malate, tartarate, citrate, ascorbate, maleate, hydroxymaleate, benzoate, hydroxybenzoate, phenylacetate, cinnamate, salicylate and 2-phenoxybenzoate. The salt may have at least one positively charged ion such as lithium, sodium, potassium, beryllium, magnesium, calcium and quaternary ammonium ions, where exemplary quaternary ammonium ions are tetraalkylammonium, and trialkylaralkylammonium ions.

The invention is also directed to the above-identified cyclic decapeptides and derivatives thereof in a pharmaceutical composition. A pharmaceutical composition of the invention may not necessarily contain the cyclic decapeptide or derivative thereof in a substantially purified form because the composition may contain diluent and/or other materials commonly found in pharmaceutical compositions, such that the above-identified cyclic decapeptides and derivatives thereof constitute less that 1 weight percent of the pharmaceutical composition.

The invention is also directed to a method of employing the compounds of the invention as an antibiotic.

DETAILED DESCRIPTION OF THE INVENTION

The invention is directed to isolated cyclic decapeptides having one of formulas (1), (2) or (3) shown below (SEQ ID NO:1, 2 and 3 respectively) and are named Loloatin A, Loloatin B and Loloatin C, respectively.

(1)

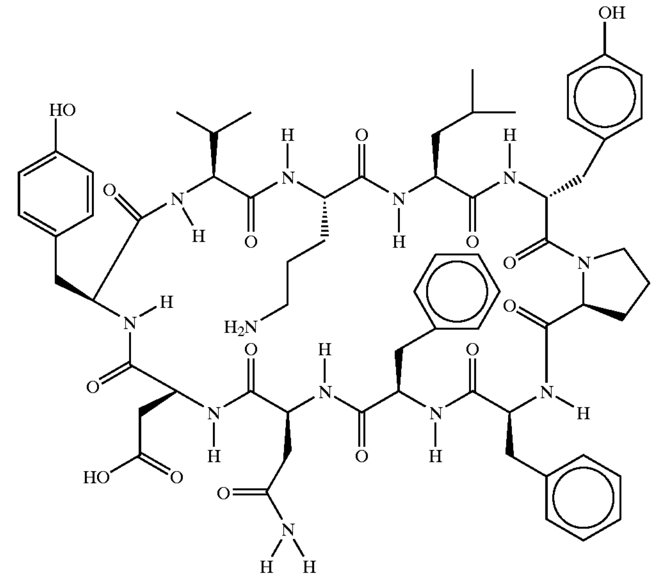

Loloatin A

-continued (2)

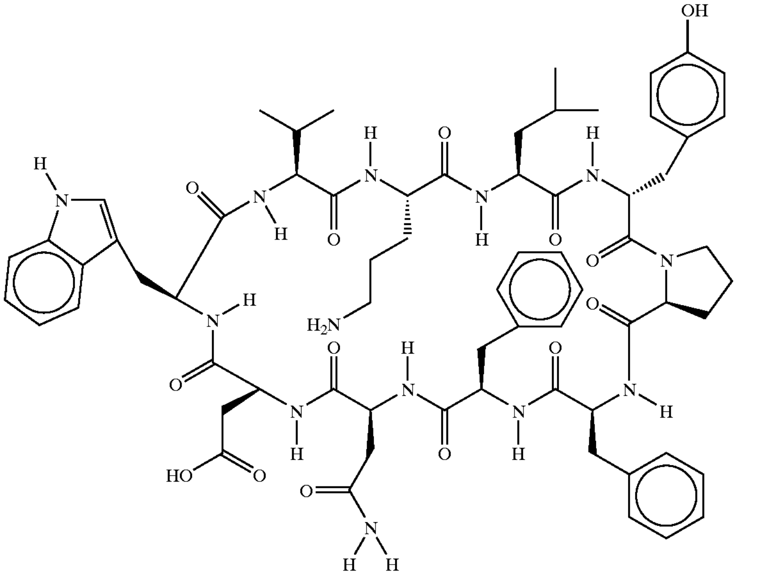

Loloatin B (3)

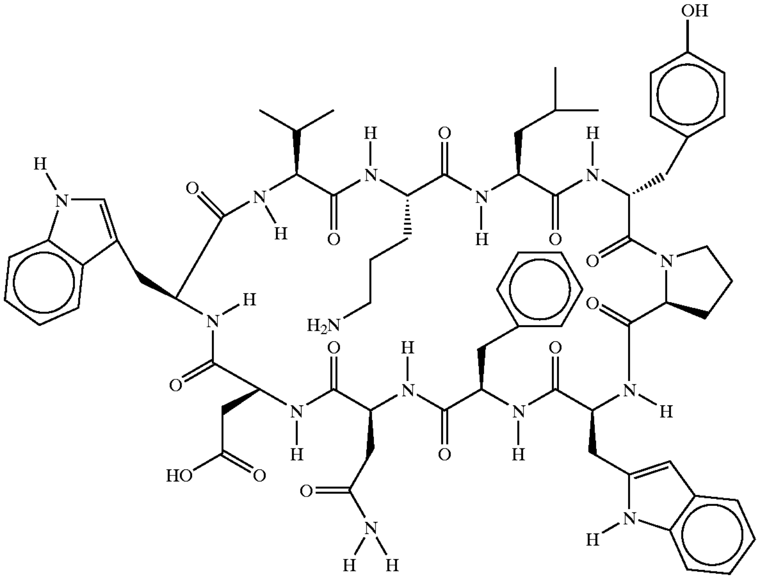

Loloatin C

Written in different terms, Loloatin A, B and C have the amino acid sequences set forth in Table A below, where the first listed amino acid is joined through a peptide bond to the last listed amino acid so as to form a cyclic structure.

TABLE A

| Loloatin A | Loloatin B | Loloatin C |
|---|---|---|
| L-Val | L-Val | L-Val |
| L-Orn | L-Orn | L-Orn |
| L-Leu | L-Leu | L-Leu |
| D-Tyr | D-Tyr | L-Tyr |
| L-Pro | L-Pro | L-Pro |
| L-Phe | L-Phe | L-Trp |

TABLE A-continued

| Loloatin A | Loloatin B | Loloatin C |
|---|---|---|
| D-Phe | D-Phe | D-Phe |
| L-Asn | L-Asn | L-Asn |
| L-Asp | L-Asp | L-Asp |
| L-Tyr | L-Trp | L-Trp |

In another aspect, the invention is directed to cyclic compounds represented by the shorthand structure shown below, denoted Formula (A).

Formula (A)

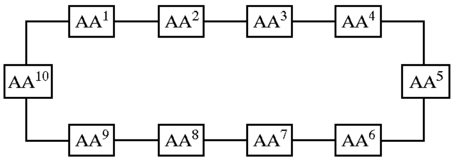

In Formula (A), $AA^1$ through $AA^{10}$ are generic symbols, each representing an amino acid residue as defined herein, or a salt or derivative thereof. Each line between neighboring (attached) $AA^1$–$AA^{10}$ residues represents an amide (also known as a peptide) bond formed between neighboring $AA^1$–$AA^{10}$ residues, as well as the isosteres thereof "Isostere" means a modified form of the normal peptide bond (—C(O)NH—) between attached amino acid residues, such as $—CH_2NH—$ (reduced), $C(O)N(CH_3)$ (N-methylamide), $—COCH_2—$ (keto), $—CH(OH)CH_2—$ (hydroxy), $—CH(NH_2)CH_2—$ (amino), $—CH_2CH_2—$ (hydrocarbon), or —NHC(O)— (inverted normal peptide bond). Preferably the compounds of the present invention are not in isosteric forms.

In Formula (A), $AA^1$–$AA^{10}$ represent residues from the following specific amino acids or other listed compounds, where stereochemical designations are preferred only, and the specifically named amino acid or other listed compound may be in either the L or D form:

$AA^1$: L-valine, butyrine;

$AA^2$: L-ornithine, L-diaminobutyric acid;

$AA^3$: L-teucine, L-isoleucine, L-alloisoleucine, L-norvaline, L-cyclopropylalanine, norleucine;

$AA^4$: D-tyrosine, p-fluorophenylalanine, tryptophan, thienylalanine;

$AA^5$: L-proline, azetidine-2-carboxylic acid, pipecolic acid, trans-3-methylproline, trans-fluoroproline;

$AA^6$: L-phenylalanine, tryptophan, tyrosine, p-fluorophenylalanine, thienylalanine, β-phenylserine;

$AA^7$: D-phenylalanine, tyrosine, p-fluorophenylalanine, tryptophan, thienylalanine, β-phenylserine;

$AA^8$: L-asparagine;

$AA^9$: L-aspartic acid or esters thereof; and $AA^{10}$: L-tryptophan, L-tyrosine, p-fluorophenylalanine, phenylalanine, thienylalanine, β-phenylserine.

The compounds of Formula (A) specifically include salts and other derivatives of the amino acids listed above. An amino acid derivative is intended to include the solvates, salts (either acid- or base- addition salts, depending on whether the amino acid sidechain is basic or acidic, respectively), esters (derivatives of amino acid sidechains containing a carboxylic acid group), amines (derivatives of amino acid sidechains containing an amino group), ethers (derivatives of amino acid sidechains containing an hydroxyl group) and amides (derivatives of amino acid sidechains containing either an amine or carboxylic acid group) of the unmodified cyclic compound. Collectively, the compounds of the invention may be referred to as compounds of Formula (A).

Except where otherwise stated, throughout this specification the recitation of a compound denotes all possible isomers within the structural formula given for those compounds, in particular optical isomers. Unless otherwise stated definitions are to be regarded as covering mixtures of isomers, and individual isomers, including racemic mixtures, where they can be resolved.

Except if otherwise stated, definitions of compounds in this specification are to be regarded as covering all possible esters of the compounds. In particular, except if otherwise stated, the recitation of an amino acid residue having a carboxylic acid group is to be regarded as a recitation of all possible esters of that carboxylic acid.

Except if otherwise stated, definitions of compounds in this specification having phenolic groups are to be regarded as covering all possible ethers or esters of the phenolic hydroxyl group.

Preferred compound of the invention have one of formulas (4), (5) or (6) shown below (SEQ ID NOS:1,2 and 3 respectively:

(4)

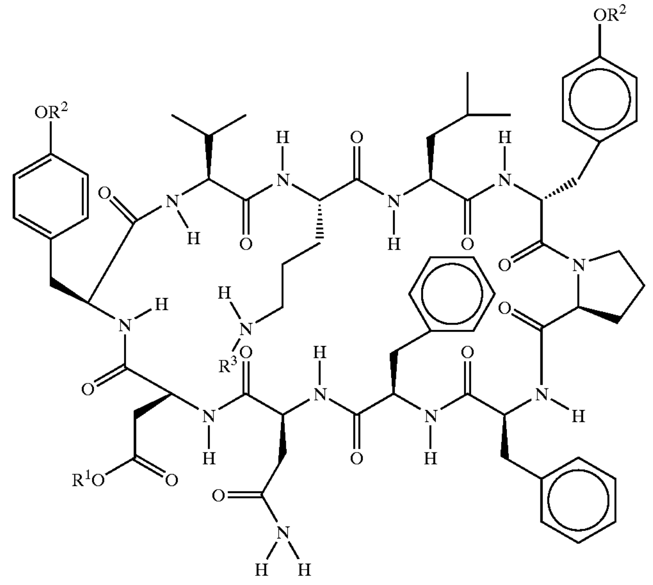

-continued (5)

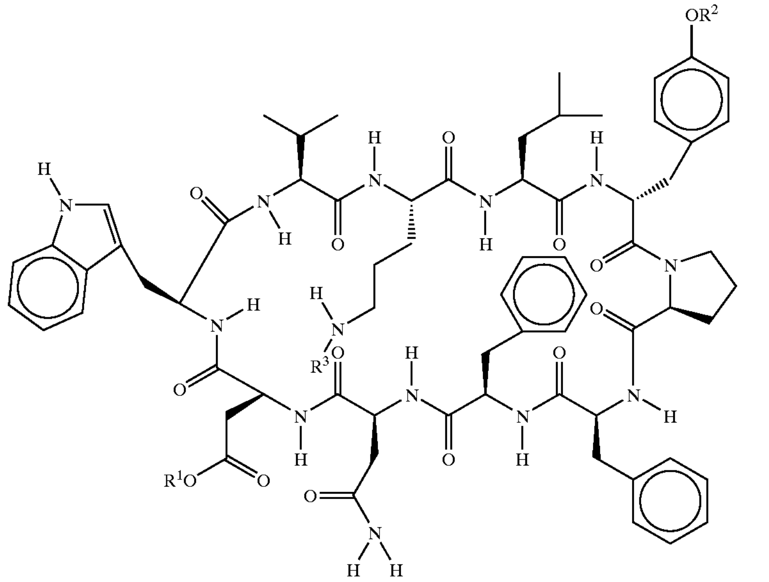

(6)

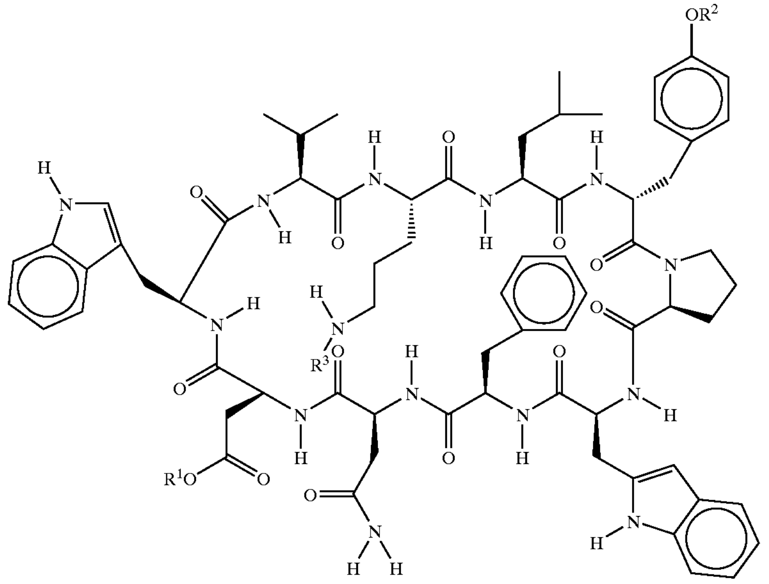

wherein $R^1$ represents a hydrogen atom; or an alkyl group that may be of straight chain, or where possible, of cyclic or branched structure and may contain one or more alkene, alkyne, or aromatic functionalities; or an aryl group.

$R^2$ represents a hydrogen atom; or an alkyl group that may be of straight chain, or where possible, of cyclic or branched structure and may contain one or more alkene, alkyne, or aromatic functionalities; or an acyl group that may be of straight chain, or where possible, of cyclic or branched structure and may contain one or more alkene, alkyne, or aromatic functionalities.

$R^3$ represents a hydrogen atom; or an alkyl group that may be of straight chain, or where possible, of cyclic or branched structure and may contain one or more alkene, alkyne, or aromatic functionalities; or an acyl group that may be of straight chain, or where possible, of cyclic or branched structure and may contain one or more alkene, alkyne, or aromatic functionalities.

The compounds of the invention may also be described in terms of Formula (B)

(B)

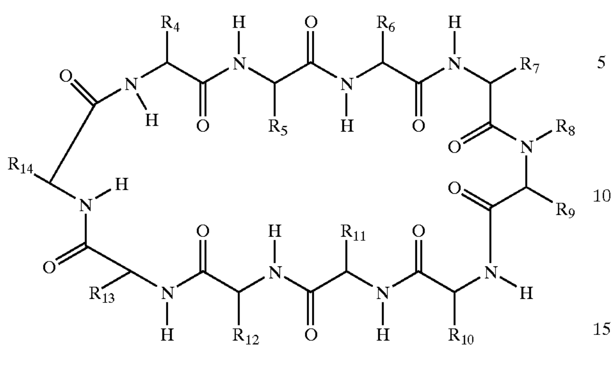

wherein:

$R^4$ is $C_{1-5}$alkyl, which may be branched or linear, or $C_{3-5}$cycloalkyl;

$R^5$ is —$(CH_2)_n$—$N(R_{15})_2$ wherein n is 1, 2, 3 or 4 and $R_{15}$ is independently hydrogen or $C_{1-15}$alkyl group that may be of straight chain, or where possible, of cyclic or branched structure and may contain one or more alkene, alkyne, or aromatic functionalities; or a $C_{1-15}$acyl group that may be of straight chain, or where possible, of cyclic or branched structure and may contain one or more alkene, alkyne, or aromatic functionalities;

$R^6$ is $C_{1-7}$alkyl, which may be branched or linear, or $C_{3-7}$cycloalkyl;

$R^7$ is $CH_2)_m$—$C_6H_4$—$OR_{16}$ wherein m is 1, 2 or 3 and $R_{16}$ is hydrogen atom; or a $C_{1-15}$ alkyl group that may be of straight chain, or where possible, of cyclic or branched structure and may contain one or more alkene, alkyne, or aromatic functionalities; or a $C_{1-15}$acyl group that may be of straight chain, or where possible, of cyclic or branched structure and may contain one or more alkene, alkyne, or aromatic functionalities, and $C_6H_4$ is an aromatic ring, and —$OR_{16}$ is in a para relationship to the $(CH_2)_m$ group;

$R^8$ and $R^9$ in combination form a 5, 6 or 7 membered ring, which may contain 1 or 2 heteroatoms selected from the group consisting of oxygen, nitrogen and sulfur, but otherwise contains only carbon and hydrogen atoms;

$R^{10}$ is —$(CH_2)_m$—$C_{6-10}$aryl, or —$(CH_2)_m$—$C_{5-9}$heteroaryl wherein the aryl and heteroaryl may be monocyclic or bicyclic, a heteroaryl contains 1 or 2 heteroatoms selected from oxygen, nitrogen and sulfur in the ring system, where $R^{10}$ specifically includes the sidechain from phenylalanine and tryptophan;

$R^{11}$ is —$(CH_2)_n$—$C_{6-10}$aryl and —$(CH_2)_n$—$C_{5-9}$heteroaryl where a heteroaryl contains 1 or 2 heteroatoms selected from oxygen, nitrogen and sulfur in the ring system, and n is 1, 2, 3 or 4;

$R^{12}$ is —$(CH_2)_n$—C(=O)$NH_2$ wherein n is 1, 2, 3 or 4;

$R^{13}$ is $(CH_2)_n$—C(=O)$OR_{17}$ wherein n is 1, 2, 3 or 4 and $R_{17}$ is a hydrogen atom; or a $C_{1-15}$alkyl group that may be of straight chain, or where possible, of cyclic or branched structure and may contain one or more alkene, alkyne, or aromatic functionalities; or an aryl group; and $R^{14}$ is selected from the groups which may be $R^7$ and $R^{10}$ as described above, with the clarification that $R^14$ need not be identically the same as either $R^7$ or $R^{10}$.

The compounds of the present invention may be prepared in vitro, using solid phase or solution peptide synthesis techniques, or may be prepared in vivo, from microorganism ATCC 55797. Solution phase techniques as set forth in K. Okamato, K. et al. *Bull. Chem. Soc. Jpn.* 50:231–236 (1977), Ohno, M. et al. *J. Am. Chem. Soc.* 88(2):376–377 and Kosui, N. et al. *Int. J. Peptide Protein Res.* 18:127–134 (1981) may be modified to prepare the cyclic decapeptides of the present invention, merely by appropriate substitution of the suitably protected amino acids. Ösapay, G.; Profit, A.; Taylor, J. W., "Synthesis of Tyrocidine A. Use of Oxime Resin for Peptide Chain Assembly and Cyclization," *Tetrahedron Letters* 131 (43):6121–6124 (1990) describes a synthetic scheme (termed PCOR for Peptide Cyclization on Oxine Resin) using a solid support, which can be modified to prepare the compounds of the present invention. The compounds of the invention may also be isolated from microorganism ATCC 55797 under appropriate conditions.

Ion exchange techniques can be used to prepare the various salts of the invention, where such techniques are well known in the art. For example, hydrochloric acid may be added to a neutral compounds of the invention to prepare the hydrochloride salt thereof. Dialysis techniques may also be employed to effect ion exchange and so obtain a desired salt of the invention from another salt of the invention.

Derivatives of Loloatin A, B and C may be prepared simply by using the corresponding derivatized amino acid in the synthesis of the cyclic decapeptide. For example, if a Loloatin A derivative having tyrosine methyl ether at the $AA^{10}$ position is desired, such a cyclic decapeptide may be prepared by the techniques described below, by substituting tyrosine methyl ether for tyrosine. Other derivatives may be made analogously by techniques known in the art. Appropriate derivatived amino acid may be prepared by techniques known in the art, or they may be purchased from any of several chemical supply houses, for example, Sigma Chemical and Bachem as identified elsewhere herein.

The Loloatins and compounds of the invention (i.e., the analogs and derivatives of Loloatins) have utility as antibiotics, and may be used and administered in a manner analogous to antibiotics known in the art, to provide the beneficial effects desired of antibiotics. Preferably, the use is in the veterinary or, more preferably, the pharmaceutical field. Thus, the invention extends to the use of any compound of Formula (A or B) or Loloatin A, B or C for the manufacture of a medicament for use in therapy. The invention further provides the use of any compound of Formula (A or B) or Loloatin A, B or C for the mire of a medicament for use in the treatment of methicillin-resistant *Staphylococcus aureus*, vancomycin-resistant. *Enterococcus faecalis*, and *Streptococcus pneumoniae* infections in a mammal. The cyclic decapeptides of the invention may be used against gram negative and gram positive bacteria.

In using a compound of Formula (A or B), or Loloatin A, B or C, the compound is preferably administered to a patient in a pharmaceutical or veterinary composition comprising also a pharmaceutically or veterinarily acceptable carrier, and optionally, one or more other biologically active ingredients. Such compositions may be in any form used for oral, topical vaginal, parenteral, rectal and inhalatory application. The compositions may be provided in discrete dose units. The carriers may be particulate, with compositions being, for example, tablets or powders, or liquid, with the compositions being, for example, oral syrups or injectable liquids, or gaseous, for inhalatory application.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed. For rectal administration oleaginous bases may be employed, for example, lanolin or cocoa butter. For an injectable formulation, buffers, stabilizers and isotonic agents may be included.

It will be evident to those of ordinary skill in the art that the optimal dosage of the compounds of Formula (A or B), or Loloatin A, B or C may depend on the weight and physical condition of the patient; on the severity and longevity of the illness; and on the particular form of the active ingredient, the manner of administration and the composition employed.

It is to be understood that use of a compound of Formula (A or B), or Loloatin A, B or C in chemotherapy can involve such a compound being bound to an agent, for example, a monoclonal or polyclonal antibody, a protein or a liposome, which assist the delivery of said compound to the site of infection.

Therefore, the invention relates further to a pharmaceutical or veterinary composition comprising an effective amount of compound of Formula (A or B), or Loloatin A, B or C in association with a carrier.

In a further embodiment, the present invention provides a method for the treatment of a patient afflicted with a bacterial infection comprising the administration thereto of a therapeutically effective amount of a compound of Formula (A or B), or Loloatin A, B or C.

The term "therapeutically effective amount" refers to an amount which is effective, upon single or multiple dose administration to the patient, in providing relief of symptoms associated with bacterial infections. As used herein, "relief of symptoms" of a bacterial infection refers to a decrease in severity over that expected in the absence of treatment and does not necessarily indicate a total elimination or cure of the infection or condition caused thereby. In determining the therapeutically effective amount or dose, a number of factors are considered by the attending diagnostician, including, but not limited to: the species of mammal; its size, age, and general health; the specific infection involved; the degree of or involvement or the severity of the infection or condition arising therefrom; the response of the individual patient; the particular compound administered; the mode of administration; the bioavailability characteristics of the preparation administered; the dose regimen selected; the use of concomitant medication; and other relevant circumstances.

A therapeutically effective amount of a compound of Formula (A or B), or Loloatin A, B or C is expected to vary from about 0.1 milligram per kilogram of body weight per day (mg/kg/day) to about 100 mg/kg/day. Preferred amounts are expected to vary from about 0.5 to about 10 mg/kg/day.

In effecting treatment of a patient afflicted with a condition described above, a compound of Formula (A or B), or Loloatin A, B or C, can be administered in any form or mode which makes the compound bioavailable in effective amounts, including oral, aerosol, and parenteral routes. For example, compounds of Formula (A or B), or Loloatin A, B or C, can be administered orally, by aerosolization, subcutaneously, intramusculary, intravenously, transdermally, intranasally, rectally, topically, and the like. Oral or aerosol administration is generally preferred. One skilled in the art of preparing formulations can readily select the proper form and mode of administration depending upon the particular characteristics of the compound selected, the condition to be treated, the stage of the condition, and other relevant circumstances. See, e.g., Remington's Pharmaceutical Sciences, 18th Edition, Mack Publishing Co. (1990).

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice.

In another embodiment, the present invention provides compositions comprising a compound of Formula (A or B), or Loloatin A, B or C, in admixture or otherwise in association with one or more inert carriers. These compositions are useful, for example, as assay standards, as convenient means of making bulk shipments, or as pharmaceutical compositions. An assayable amount of a compound Formula (A or B), or Loloatin A, B or C, is an amount which is readily measurable by standard assay procedures and techniques as are well known and appreciated by those skilled in the art. Assayable amounts of a compound Formula (A or B), or Loloatin A, B or C, will generally vary from about 0.001% to about 75% of the composition by weight. Inert carriers can be any material which does not degrade or otherwise covalently react with a compound of Formula (A or B), or Loloatin A, B or C,. Examples of suitable inert carriers are water, aqueous buffers, such as those which are generally useful in High Performance Liquid Chromatography (HPLC) analysis, organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of Formula (A or B), or Loloatin A, B or C, in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention. The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The compounds of Formula (A or B), or Loloatin A, B or C, of the present invention may also be administered by aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of Formula (A or B), or Loloatin A, B or C, may be delivered in single phase, bi-phasic, or tri-phasic systems in order to deliver the active ingredient. Delivery of the aerosol includes the necessary container, activators, valves, subcontainers, and the like. Preferred aerosols are able to be determined by one skilled in the art.

The compounds of Formula (A or B), or Loloatin A, B or C, of this invention may also be administered topically, and when done so the carrier may suitably comprise a solution, ointment or gel base. The base, for example, may comprise one or more of the following: petrolatum, lanolin, polyethylene glycols, bee wax, mineral oil diluents such as water and alcohol, and emulsifiers and stabilizers. Topical formulations may contain a concentration of the Formula (A or B), or Loloatin A, B or C, compound of from about 0.1 to about 10% w/v (weight per unit volume).

The solutions or suspensions may also include one or more of the following adjuvants: sterile diluents such as water for injection, saline solution, fixed oils, polyethylene glycols, glycerin, propylene glycol or other synthetic solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The cyclic decapeptides of the invention may be combined with one or more known antibiotics to provide a synergistic composition. In other words, a composition comprising a cyclic decapeptide of the invention and a known antibiotic may have greater efficacy against bacteria than would be expected based on the individual efficacies of the cyclic decapeptide and the known antibiotic.

As used herein, the term "patient" refers to a warm-blooded animal such as a mammal which is afflicted with a particular inflammatory disease state. It is understood that guinea pigs, dogs, cats, rats, mice, horses, cattle, sheep, and humans are examples of animals within the scope of the meaning of the term.

The following examples are offered by way of illustration and not by way of limitation.

EXAMPLES

Symbols and abbreviations used herein are in accordance with the recommendation of IUPAC-IUB Commissioner on Biochemical Nomenclature, *J. Biol. Chem.* 1971, 247, 977. Abbreviations: "Asn" refers to asparagine; "Asp" refers to aspartic acid, "bp" refers to boiling point; BOP=benzotriazol-1-yl-oxy-tris-(dimethylamino) phosphonium hexafluorophosphate; "BrZ" refers to bromobenzyloxycarbonyl; "Bzl" refers to benzyl; "° C" refers to degrees Celsius; CD=circular dichroism; "DCC" refers to N,N-dicyclohexylcarbodiimide; DCM=dichloromethane, DIEA=N,N-diisopropylethylamine; DMF=N,N-dimethylformamide; "DPPA" refers to diphenylphosphorylazide; FAB-MS=fast atom bombardment mass spectrometry; "HOBt" refers to 1-hydroxybenzotriazole; "g" refers to grams; "Leu" refers to leucine; "mL" refers to milliliters; "mm Hg" refers to millimeters of mercury; "mmol" refers to millimoles; "NMP" refers to N-methylpyrrolidinone; "Orn" refers to ornithine; "Phe" refers to phenylalanine; "Pro" refers to proline; "TEA" refers to triethylaine; TMSOTf=trimethylsilyl trifiuoromethanesulfonate; "Tos" refers to p-toluenesulfonyl;. "Trp" refers to tryptophan; "Tyr" refers to tyrosine; "Val" refers to valine, Z=benzyloxycarbonyl; "$\mu$g" refers to micrograms; "$\mu$L" refers to microliters; and "$\mu$M" refers to micromolar.

A. PREPARATIVE EXAMPLES

The cyclic decapeptides of the present invention may be prepared in vitro, using solid phase or solution peptide synthesis techniques, or may be prepared in vivo, from microorganism ATCC 55797. Solution phase techniques as set forth in K. Okamato, K. et al. *Bull. Chem. Soc. Jpn.* 50:231–236 (1977), Ohno, M. et al. *J. Am. Chem. Soc.* 88(2):376–377 and Kosui, N. et al. *Int. J. Peptide Protein Res.* 18:127–134 (1981) may be modified to prepare the cyclic decapeptides of the present invention, merely by appropriate substitution of the suitably protected amino acids.

The following examples present typical syntheses. These examples are understood to be illustrative only and are not intended to limit the scope of the present invention in any way.

Example A1

Ösapay, G.; Profit, A.; Taylor, J. W., "Synthesis of Tyrocidine A: Use of Oxime Resin for Peptide Chain Assembly and Cyclization," *Tetrahedron Letters* 131(43):6121–6124 (1990) describes a synthetic scheme (termed PCOR for Peptide Cyclization on Oxime Resin) using a solid support, which can be modified to prepare the cyclic decapeptides of the present invention. Further details of the PCOR method may be found in Ösapay, G.; Bouvier, M.; Taylor, J. W., "Peptide Cyclization on Oxime Resin (PCOR)" in Techniques in Protein Chemistry II, (ed. Villafranca, J. J.). The following description illustrates the synthesis of Loloatin A.

The p-nitrobenzophenone oxime polymer described by DeGrado and Kaiser may be used as a solid support in preparing cyclic decapeptides of the present invention. See DeGrado, W. F.; Kaiser, E. T., *J. Org. Chem.* 45:1295–1300

(1980). For the preparation of for example, cyclo[L-Val-L-Orn-L-Leu-D-Tyr-L-Pro-L-Phe-D-Phe-L-Asn-L-Asp-L-Tyr] (Loloatin A) the starting compound Boc-Leu-resin is the same as described in the Ösapay article, and the excess oxime groups may be capped by acetylation as described therein. The peptide chain may be assembled by consecutive addition of the following $N^{\alpha}$-Boc-amino acids, which have the L-configuration unless otherwise noted: BocOrn(Z)OH, BocValOK BocTyr(2,6-$Cl_2$-Bzl)OH, BocAsp(β-Bzl)OH, BocAsnOH, Boc-D-PheOH BocPheOH, BocProOH and BocTyr(2,6-$Cl_2$-Bzl)OH, all according to the BOP peptide coupling procedure of Fournier, A.; Wang, C. T.; Felix, A. M., *Int. J. Pept., Prot. Res.*; 31:86–97 (1988).

Boc protecting groups may be removed by treatment with 25% TFA/DCM solution for 30 minutes. After the appropriate washing steps, Boc-amino acids and BOP reagent may be added in 5-fold excess in DMF solution followed by the same excess of DIEA. After a 2-hour reaction time, the completeness of each coupling may be monitored by the Kaiser test. See Kaiser, E.; Colescott, R. L.; Cook, P. I., *Anal Biochem.*, 34:595–598 (1970). Coupling of BocAsnOH may be repeated with 2.5 molar equivalent reagent to insure a high yield of the product.

After final removal of the Boc protecting group from the N terminus, the amino group may be liberated from its TFA salt by addition of DIEA (1.5 equivalents). The free amino group may cleave the peptide from the polymer support by intrachain aminolysis in DCM at room temperature. After a 24 hour reaction time, the product may be obtained from the solution phase by filtration. This crude product may be purified by silica gel chromatography (e.g., 2×20 cm, eluent $CHCl_3$/MeOH/AcOH=18/1/1).

Protecting groups of the peptide may be removed with TMSOTf in TFA in the presence of thioanisole, according to the procedure of Fujii, N. et al., *J. Chem. Soc., Chem. Commun.*, 274–275 (1987). Hydrolysis of the partly silylated product by $NH_4OH$ may be followed by gel permeation chromatography, for example, using Sephadex G-10 column (eluent, e.g.,: 2 M acetic acid in $H_2O$/MeOH, 4/1 [v/v]). Final purification may be carried out by RP-HPLC on, for example, a Vydac $C_{18}$ Proteins semi-preparative column eluted at, e.g., 4 mL/min with a linear gradient of 25%–80% acetonitrile in 0.1% (v/v) TFA over 45 minutes.

In the above-described synthesis, one or more of the $N^{\alpha}$-Boc-amino acid starting materials may be purchased from chemical supply houses, for example, Sigma Chemical Company, PO Box 14508, St. Louis, Mo. 63178 (Sigma's "Peptides and Amino Acids" catalog provides a convenient listing) and Bachem, 6868 Nancy Ridge Dr., San Diego, Calif. 92121.

Example A2

The preparation of Loloatin B follows the synthesis of Loloatin A as described in Example A1, with the exception that BocTyr(2,6-$Cl_2$-Bzl)OH is replaced with BocTrp(Z)OH or other sidechain amine-protected L-tryptophan.

Example A3

The preparation of Loloatin C follows the synthesis of Loloatin B as described in Example A2, with the exception that BocPheOH is replaced with BocTrp(Z)OH or other sidechain amine-protected L-tryptophan.

Example A4

Solid phase peptide synthesis according to the method originally described by Merrifield, *J. Am Chem. Soc.* 85:2149–2154, 1963, the disclosure of which is hereby incorporated by reference, may be used to prepare the linear analogs of the cyclic decapeptides of the invention. Alternatively, solution synthesis may be used to prepare these linear peptide analogs. Generally, peptides may be elongated by deprotecting the α-amine of the C-terminal residue and coupling the next suitably protected amino acid through a peptide linkage using the methods described. This deprotection and coupling procedure is repeated until the desired sequence is obtained. This coupling can be performed with the constituent amino acids in stepwise fashion, or by condensation of fragments (two to several amino acids), or combination of both processes, or by solid phase peptide synthesis as stated above. Thereafter, the linear peptides may be cyclized by well known peptide cycliation techniques, to prepare the cyclic decapeptides of the invention.

When a solid phase synthetic approach is employed, the C-terminal carboxylic acid is attached to an insoluble carrier (usually polystyrene). These insoluble carriers contain a group which will react with the α-carboxyl group to form a bond which is stable to the elongation conditions but readily cleaved later. Examples of which include: chloro- or bromomethyl resin, hydroxymethyl resin, and aminomethyl resin. Many of these resins are commercially available with the desired C-terminal amino acid already incorporated. Many of the suitably protected amino acids used in the present invention are also available commercially from Sigma Chemical Company and Bachem.

Alternativey, compounds of the invention can be synthesized using automated peptide synthesizing equipment. In addition to the foregoing, peptide synthesis are described in Stewart and Young, "Solid Phase Peptide Synthesis," 2nd ed., Pierce Chemical Co., Rockford, Ill. (1984); Gross Meienhofer, Udenfriend, Eds., "The Peptides: Analysis, Synthesis, Biology," Vol. 1, 2, 3, 5 and 9, Academic Press, New York, 1980–1987; Bodanszky, "Peptide Chemistry: A Practical Textbook," Springer-Verlag, N.Y. (1988); and Bodanszky et al., "The Practice of Peptide Synthesis," Springer-Verlag, N.Y. (1984), the disclosures of which are hereby incorporated by reference.

Coupling between two amino acids, an amino acid and a peptide, or two peptide fragments can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxy-succinic imido ester) method, Woodward reagent K method, carbonyldiimidazole method, phosphorus reagents such as BOP-Cl, or oxidation-reduction methods. Some of these methods (especially the carbodiimide method) can be enhanced by adding 1-hydroxybenzotriazole. These coupling reactions can be performed in either solution (liquid phase) or solid phase.

The functional groups of the constituent amino acids must be protected during the coupling reactions to avoid formation of undesired bonds. The protecting groups that can be used are listed in Greene, "Protective Groups in Organic Chemistry," John Wiley & Sons, New York (1981) and "The Peptides: Analysis, Synthesis, Biology," Vol. 3, Academic Press, New York (1981), the disclosures of which are hereby incorporated by reference.

The α-carboxyl group of the C-terminal residue is usually protected by an ester that can be cleaved to give the carboxylic acid. Protecting groups which can be used include: (1) alkyl esters such as methyl and t-butyl, (2) aryl esters such as benzyl and substituted benzyl, or (3) esters which can be cleaved by mild base treatment or mild reductive means such as trichloroethyl and phenacyl esters.

The α-amino group of each amino acid must be protected. Any protecting group known in the art can be used. Examples of which include: (1) acyl types such as formyl, trifluoroacetyl, phthalyl, and p-toluenesulfonyl; (2) aromatic carbamate types such as benzyloxycarbonyl (Cbz or Z) and substituted benzyloxycarbonyls, 1-(p-biphenyl)1, -methylethoxy-carbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; and (7) thiol containing types such as phenylthiocarbonyl and dithiasuccinoyl. The preferred α-amino protecting group is either Boc or Fmoc, preferably Fmoc. Many amino acid derivatives suitably protected for peptide synthesis are commercially available.

The α-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidine in dimethylformamide, but any secondary amine or aqueous basic solutions can be used. The deprotection is carried out at a temperature between 0° C. and room temperature.

Any of the amino acid bearing side chain functionalities must be protected during the preparation of the peptide using any of the above-described groups. Those skilled in the art will appreciate that the selection and use of appropriate protecting groups for these side chain functionalities depends upon the amino acid and presence of other protecting groups in the peptide. The selection of such protecting groups is important in that it must not be removed during the deprotection and coupling of the α-amino group. For example, when Boc is used as the α-amino protecting group, p-toluenesulfonyl (tosyl) moieties can be used to protect the amino side chain of Orn. When Fmoc is chosen for the α-amine protection usually tert-butyl based protecting groups are acceptable. For instance, Boc can be used for ornithine.

Once the elongation of the peptide is completed all of the protecting groups are removed. When a solution phase synthesis is used, the protecting groups are removed in whatever manner is dictated by the choice of protecting groups. These procedures are well known to those skilled in the art.

When a solid phase synthesis is used, the peptide is cleaved from the resin usually simultaneously with the protecting group removal. When the Boc protection scheme is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acidic reagents such as trifluoromethanesulfonic acid/trifluoroacetic acid mixtures. If the Fmoc protection scheme is used, the N-terminal Fmoc group is cleaved with reagents described earlier. The other protecting groups and the peptide are cleaved from the resin using a solution of trifluoroacetic acid and various additives such as anisole, etc.

Subsequent to removal of the linear peptide from the resin and removal of any protecting groups as desirable, the linear peptide is cyclized using conventional procedures such as by treatment with triethylamine and diphenylphosphorylazide in dimethylformamide. Prior to purification of the crude cyclic peptide in the usual manner such as by use of chromatography, any remaining protecting and functional group precursors are removed or transformed into the desired group.

Example A4a

Synthesis of cyclo[L-Val-L-Orn-L-Leu-D-Tyr-L-Pro-L-Phe-D-Phe-L-Asn-L-Asp-Lyr] (Loloatin A) (SEQ ID NO:1).

Synthesis of the Linear Peptide

The linear analog of Loloatin A may be synthesized by standard solid phase methods using an Applied Biosystems (850 Lincoln Centre Dr., Foster City, Calif.) 430A automated peptide synthesizer and protocols supplied by the manufacturer. Commercially available Boc-amino acids may be used with the following side chain protection: Orn(Tos), Tyr(BrZ), Asp(Bzl). Commercially available Boc-Val-PAM resin (0.5 mmol, Applied Biosystems) may be deprotected with trifluoroacetic acid (2% anisole) and coupled in NMP with the HOBt esters of Boc-amino acids (4 equivalents). The HOBt esters of Boc-amino acids may be formed by the reaction of the Boc-amino acid with DCC and HOBt. Couplings may be carried out for 30 minutes and the resin subsequently washed with NMP and DCM. Any unreacted amine may be acylated with acetic anhydride. The deprotection and coupling may be repeated until complete assembly of the protected peptide resin is achieved. The linear peptide may be simultaneously deprotected and removed from the resin with anhydrous hydrogen fluoride (10 mL) at 0° C. for 30 minutes in the presence of anisole (5%). The peptide may then be extracted with 50% acetic acid, water and aqueous acetonitrile, and lyophilized.

Cyclization of the Linear Peptide

The crude linear peptide prepared above may be dissolved in DMF (~5 μmol/ml) and cyclized with DPPA (5 equivalents) TEA to adjust the pH to 9. After completion of the reaction (4–48 hours), the solvent may be removed and the crude cyclic peptide lyophilized from acetonitrile/water. The cyclic peptide may then be desalted by gel filtration in, e.g., 70% acetic acid over a Spectragel GF05 column (2.5×55 cm), and purified by reversed phase preparative HPLC (Dynamax $C_{18}$, 21.4×250 mm, Rainin) using various gradients of 0.1% aqueous TFA and acetonitrile.

The purified peptide may then be characterized by Analytical HPLC (Vydac 218TP54, 4.6×250 mm), FAB-MS and amino acid analysis, and these characterizations compared to theoretical values when available.

Example A5

The procedure of Example A4a may be modified to prepare Loloatin B. Thus, when Tyr(BrZ) is replaced with Trp(Z) or other amine-protected L-tryptophan, Loloatin B may be prepared.

Example A6

The procedure of Example A5 may be modified to prepare Loloatin C. Thus, when Phe is replaced with Trp(Z) or other amine-protected L-tryptophan, Loloatin C may be prepared.

Example A7

Each of Loloatin A, B and C may be isolated after fermentation of ATCC 55797 as described below.

The marine bacterial isolate MK-PNG-276A, tentatively identified as a *Bacillus laterosporus* by MIDI analysis of cellular fatty acids, was obtained from the tissues of an unidentified tube worm collected at −15 m off of Loloata Island, Papua, New Guinea. MK-PNG-276A has been deposited with the American Type Culture Collection as ATCC 55797.

MK-PNG-276A was cultured on trays of solid tryptic soy agar supplemental with NaCl to a concentration of 1%. Twenty-six 400 mL trays (9"×15"×¼" deep agar) were cultured for five days after which the combined cells and agar were lyophilized. The lyophilization product, (61.5 g dry weight) was extracted with three 600 mL portions of methanol that were combined, filtered, and reduced in vacuo to give a brown/gray tar. The tar was dissolved in 750 mL of MeOH/$H_2O$ (¼) and sequentially extracted with hexanes (3×250 mL) and EtOAc (3×250 mL). The combined EtOAc extracts were reduced in vacuo to give a taupe/brown crystalline solid (5.5 g). The EtOAc residue was then processed in batches. Size separation on an LH-20 Sephadex column with methanol eluant gave six fractions. The first and major fraction showed antibiotic activity against MRSA and Enterococci species. This fraction was then subjected to preparative reverse phrase column chromatography and RP HPLC using 9:1 methanol/water containing 0.1% TFA, to yield Loloatin A (relative retention time on HPLC=0.70, white powder 281 mg, 0.45% dry wt of cells), Loloatin B (relative retention time on HPLC=1.00, tan/white powder solid 1.87 g, 3.0% dry wt of cells) and Loloatin C (relative retention time on HPLC=0.66, tan/white powder 40 mg, 0.065% dry wt of cells).

Loloatin B (2) gave a (M+H) ion in the HRFABMS at m/z 1296.64232 appropriate for a molecular formula of $C_{67}H_{85}N_{13}O_{14}$ (ΔM+0.46 ppm). Detailed analysis of the $^1$H, $^{13}$C, COSY, HOHAHA, HMQC, HMBC and ROESY data for Loloatin B (2) identified the ten amino acids residues indicated in Table 1. Hydrolysis of 2 at 100° C. with 6N HCl containing thioglycolic acid and examination of the pentafluropropionamide isopropyl ester derivatives of the liberated amino acids via chiral GC analysis confirmed the presence of L-valine, L-ornithine, L-leucine, D-tyrosine, L-proline, L-phenylalanine, D-phenylalanine, L-tryptophan and L-aspartic acid (from ASP and ASN). The ten identified amino acid residues accounted for all of the atoms in the molecular formula of (2), and 31 of the 32 sites of unsaturation demanded by the molecular formula. Thus, Loloatin B (2) had to be a monocyclic decapeptide.

The amino acid sequence in (2) was determined by analysis of HMBC and ROESY data HRFABMS and MS/MS studies supported the amino acid sequence derived from the NMR data. The MS/MS data was consistent with initial cleavage of the ring at the TYR-CO/PRO-N bond to give a linear decapeptide LEU-TYR (m/z 1019), ORN-LEU-TYR (m/z 905) and TRP-VAL-ORN-TYR (SEQ ID NO:78) (m/z 621). FABMS peaks at m/z 245 and 377 could be assigned to the protonated fragments PRO-PHE1 and PHE2-ASN-ASP, respectively.

The amino acid sequences for Loloatin A and C were determined in an analogous manner.

TABLE 1

$^1$H NMR Data (500 MHz) for Loloatin B (2) (DMSO-$D_6$)

| Res. | | δ $^{1H}$ |
|---|---|---|
| VAL | NH | 7.52(d, J=8.0) |
| | αCH | 4.56(m) |
| | βCH | 2.01(sept, J=7.0) |
| | γ$CH_3$ | 0.93(d) |
| | γ$CH_3$ | 0.93(d) |
| | CO | — |
| ORN | NH | 8.88(d,J=8.9) |
| | αCH | 5.27(bm) |
| | β$CH_2$ | 1.8(m) |
| | γ$CH_2$ | 1.7(m) |
| | δ$CH_2$ | 2.8, 2.9(m) |
| | δNH | 7.45(bs) |
| | CO | — |
| | $CH_3$ | |
| | CO | |
| LEU | NH | 7.92(bs) |
| | αCH | 4.55(m) |
| | β$CH_2$ | 1.35(m) |
| | | 1.25(m) |
| | γCH | 1.5(m) |
| | δ$CH_3$ | 0.93(d) |
| | δ$CH_3$ | 0.93(d) |
| | CO | — |
| TYR | NH | 9.21(s) |
| | αCH | 4.22(m) |
| | β$CH_2$ | 2.70(m) |
| | | 2.81(m) |
| | iC | — |
| | oCH | 6.98(d, J=8.6) |
| | mCH | 6.61(d, J=8.6) |
| | pCOH | not observed |
| | CO | — |
| PRO | N | — |
| | αCH | 4.07(d, J=7.6) |
| | β$CH_2$ | 1.43(m) |
| | | 1.25(m) |
| | γ$CH_2$ | 1.07(m) |
| | | 0.411(m) |
| | δ$CH_2$ | 2.20(m) |
| | | 3.30(m) |
| | CO | — |
| PHE1 | NH | 7.23(d, J=9.5) |
| | αCH | 4.5(m) |
| PHE1 | $CH_2$ | 2.25(m) |
| | iC | — |
| | oCH | 7.18 |
| | mCH | |
| | pCH | |
| | CO | — |
| PHE2 | NH | 9.05(d, J=9.0) |
| | αCH | 5.57(bt) |
| | β$CH_2$ | 2.75(m) |
| | | 3.02(m) |
| | iC | — |
| | oCH | 7.18 |
| | mCH | |
| | pCH | |
| | CO | — |
| ASN | NH | 9.03(d, J=6.0) |
| | αCH | 4.49(m) |
| | β$CH_2$ | 3.37(m) |
| | | 3.0(m) |
| | CO | — |
| | $NH_2$ | 8.04(bs) |
| | | 7.45 |
| | CO | — |
| ASP | NH | 8.32(d, J=4.2) |
| | αCH | 4.26(m) |
| | β$CH_2$ | 2.35(m) |

TABLE 1-continued

| $^1H$ NMR Data (500 MHz) for Loloatin B (2) (DMSO-$D_6$) | | |
|---|---|---|
| Res. | | δ $^{1H}$ |
| | | 2.25(m) |
| | γCO | — |
| | $CH_3$ | |
| | CO | — |
| TRP | NH | 8.63(d, J=9.8) |
| | αCH | 4.5(m) |
| | $βCH_2$ | 3.15(m) |
| | C | — |
| | C | — |
| | CH | 7.5 |
| | CH | 7.0 |
| | CH | 7.03(m) |
| | CH | 7.32(J=8.0) |
| | C | — |
| | NH | 10.81(bs) |
| | CH | 7.02(d) |
| | CO | — |

Example A8

Fermentation techniques with the microoganism ATCC 55797 may be used to obtain the cyclic decapeptides of Formulas 1, 2 and 3 as described in Example A7. Thereafter, the cyclic decapeptides of Formulas 1, 2 and 3 may be derivatized to form salts (either acid- or base- addition salts, depending on whether the amino acid sidechain is basic or acidic, respectively), esters (from amino acid sidechains containing a carboxylic acid group), amines (from amino acid sidechains containing an amino group), ethers (from amino acid sidechains containing an hydroxyl group) and amides (from amino acid sidechains containing either an amine or carboxylic acid group) of the invention.

N-acetyl loloatin B methyl ester (276bs2): Loloatin B (276bs1) (100 mg) was acetylated under argon, at 23° C. for 16 hours, using 2 mL of acetic anhydride and 1 mL anhydrous pyridine (freshly distilled). The solution was reduced in vacuo and the crude acetylated material was then loaded onto a reverse phase ODS sep-pak™ using 5 mL of 1:1 methanol/water, followed by elution with 5 mL of methanol. The methanol eluant was reduced in vacuo, dissolved in 5 mL tetrahydrofuran and reacted with diazomethane in a micro molar generator using a dry ice/acetone bath to cool the THF solution. N-acetyl loloatin B methyl ester (276bs2) was purified using reverse phase ODS HPLC with 17:3 methanol/water as eluant to yield 30 mg of N-acetyl loloatin B methyl ester.

Melting point: 229–233° C.; IR (Nujol mull) $υ_{max}$: 3278 (br,m), 3032 (m), 3065 (w), 1636 (s), 1537 (s), 1251 br,m); $[a]_D$-62.7 (ETOH); UV (EtOH) $λ_{max}$ (e): 276 (13,000), 228 (45,800), 222 (52,600), 218 (52,900), 214 (47,500), 208 (36,100); HRFABMS (M+H) m/z 1296.64232 ($C_{67}H_{86}N_{13}O_{14}$; ΔM 0.46 ppm). Chiral GC analysis of a 6N HCl hydrolysate of loloatin B identified L-leucine, L-proline, L-phenylalanine, D-phenylaline, L-ornithine, L-valine, L-tryptophan, D-tyrosine, L-aspartic acid, and L-asparagine.

FIG. 1

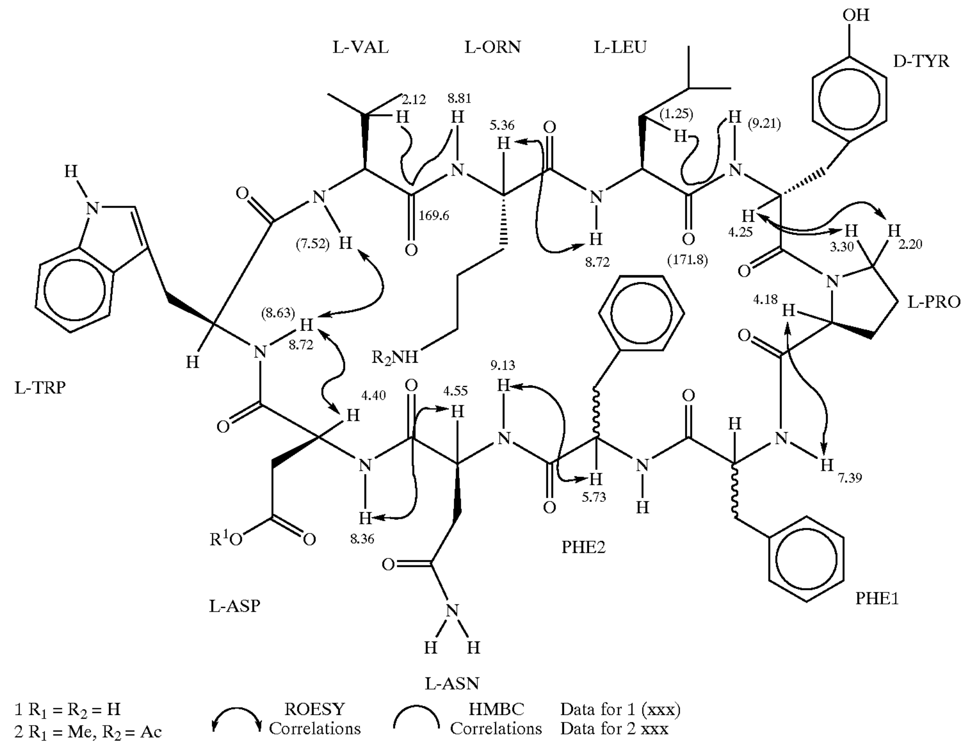

Loloatin B (2) gave a (M+H) ion in the HRFABMS at m/z 1296.64232 appropriate for a molecular formula of $C_{67}H_{85}N_{13}O_{14}$ (ΔM+0.46 ppm). Detailed analysis of the $^1H$, $^{13}C$, COSY, HOHAHA, HMQC, HMBC and ROESY data for loloatin B (2) and its N-acetyl methyl ester derivative (7), identified the ten amino acids residues indicated in Table 1. Hydrolysis of 2 at 100° C. with 6N HCl containing thioglycolic acid and examination of the pentafluropropionamide isopropyl ester derivatives of the liberated amino acids via chiral GC analysis confirmed the presence of L-valine, L-ornithine, Leucine, D-tyrosine, L-proline, L-phenylalanine, D-phenylalanine, L-tryptophan and L-aspartic acid (from ASP and ASN). The ten identified amino acid residues accounted for all of the atoms in the molecular formula of (2), and 31 of the 32 sites of unsaturation demanded by the molecular formula. Thus, loloatin B (2) had to be a monocyclic decapeptide.

The amino acid sequence in (2) was determined by analysis of the HMBC and ROESY data for both (2) and (7), as shown in FIG. 1. ROESY correlations observed in (7) between amino acid α-methine protons and adjacent residue NH protons unambiguously identified the following five amino bonds: ORN-CO/LEU-NH (δ 5.36/8.22), ASP-CO/TRP-NH (δ 4.40/8.72), ASN-CO/ASP-NH (δ 4.55/8.36), PHE2-CO/ASN-NH (δ 5.73/9.13) and PRO-CO/PHE1-NH (δ 4.18/7.39). A ROESY correlation observed between the TYR (α-methine resonance at δ 4.25 and the PRO δ-proton resonance at δ 3.30 in 7 identified the TYR-CO/PRO-N amide bond, and a strong ROESY correlation between the VAL-NH resonance at δ 7.52 and the TRP-NH resonance at δ 8.63 in 2 identified the TRP-CO/VAL-NH amide linkage. The latter ROESY correlation suggests the possibility of a β-bulge in the TRP/VAL region of the cyclic peptide as shown in FIG. 1. See, e.g., Kuo, M. et al., *J. Am. Chem. Soc.* 102:520–24, 1980; Eggleston, D. S. et al., *J. Am. Chem. Soc.* 113:4410, 1991; and Peishoff, C. E. et al., *J. Am. Chem. Soc.* 113:4416, 1991. HMBC correlations from both the VAL β-methine proton resonance at δ 2.12 and the ORN-NH resonance at δ 8.81 to the well resolved carbonyl resonance at δ 169.6 in derivative 7 identified the VAL-CO/ORN-NH amide bond, and HMBC correlations from both the LEU δ methylene proton resonance at δ 1.25 and the TYR-NH resonance at δ 9.21 to the carbonyl resonance at δ 171.8 in 2 identified the LEU-CO/T-NH amide bond. The final PHE1-CO/PHE2-NH amide bond was required to complete the macrocyclic ring.

BRFABMS and MS/MS studies supported the amino acid sequence derived from the NMR data. The MS/MS data was consistent with initial cleavage of the ring at the TYR-CO/PRO-N bond to give a linear decapeptide that sequentially loses LEU-TYR (m/z 1019), ORN-LEU-TYR (m/z 905) and TRP-VAL-ORN-LEU-TYR (m/z 621). FABMS peaks at m/z 245 and 377 could be assigned to the protonated fragments PRO-PHE1 and PHE2-ASN-ASP, respectively.

Example A9

Precursor directed biosynthesis, wherein a culture media containing the microorganism isolated in Example A7 is supplemented with a replacement amino acid at fairly high concentrations, may be used to prepare cyclic decapeptides of the invention. See, e.g., Katz, E. and Demain, A. L., "The Peptide Antibiotics of Bacillus: Chemistry Biogenesis, and Possible Functions," *Bacteriological Reviews*, June 1977, pp. 449–474.

The culture media described in Example A7 can be employed in precursor directed biosynithesis to prepare the analogs of Loloatin A, B and C by providing to the microorganism ATCC 55797 fairly high concentrations of the following amino acids. Butyrine may replace valine. L-diaminobutyric acid may replace ornithine. Any of L-isoleucine, L-alloisoleucine, L-norvaline, L-cyclopropylalanine and norleucine may replace leucine. Any of p-fluorophenyalanine, tryptophan and thienylalanine may replace tyrosine. Any of azetidine-2-carboxylic acid, pipecolic acid, trans-3-methylproline and trans-4-fluoroproline may replace proline. Any of tyrosine, p-fluorophenyalanine, tryptophan, thienylalanine and β-phenylserine may replace phenylalanine. Any of tyrosine, p-fluorophenyalanine, phenylalanine, thienylalanine and β-phenylserine may replace tryptophan.

Example A10

Synthesis of Loloatin B

Linear precursors were prepared, and then those precursors were cyclized to provide Loloatin B. The structure of the linear precursor is selected in order that the geometry of the linear sequence will bring together the N- and C- termini, thus favoring the cyclization reaction. The linear precursor was prepared by standard solid phase peptide synthesis (i.e., typical coupling and cleavage conditions), using a standard peptide acid resin (Wang), to provide:

$NH_2$ OL dY PF dF NDWV-COOH

Several cyclization chemistries were explored with this filly deprotected linear peptide precursor.

| | | | |
|---|---|---|---|
| A. | NHS-Osu | | yields very slow reaction |
| | EDC | | multiple products |
| B. | HOBT/EDC | | multiple, very hydrophobic |
| | 10 equiv, very dilute | | products (oligomers) |
| C. | HOBT | 4 equiv | 0.5 mg/ml, 20% DMF/methylene chloride |
| | EDC | 5 equiv | 4 hourly additions of equal aliquots. |
| | | | Cleanest of the conditions. |

The complex reaction mixture from Method C was chromatographed on reverse phase HPLC, and a microtiter plate assay was run throughout the entire chromatogram to identify active materials. Only one fraction, fr 73, (1 mg yield of starting 100 mg) exhibited the desired biological activity.

| | In-vitro Microbiology | | | |
|---|---|---|---|---|
| | MRSA 034 | | P.a. 028 | |
| | MIC | MBZ | MIC | MBZ |
| Fraction 73 | 8.0 | 8.0 | >128 | >128 |

Fraction 73 was identified as Loloatin B by mass spectroscopy and NMR spectroscopy. Fraction 73 did not have a free N-terminal amino group.

Loloatin B was also prepared from the following precursor, which was prepared by standard solid-phase synthesis techniques:

dF NDWVOL dY PF-COOH

The cyclization of this compound was carried out as in Method C. With this compound, cyclization proceeded much more slowly and yielded proportionately more lower r.t. materials than the first cyclization and less of the materials in the desired portion of the chromatogram.

B. ACTIVITY EXAMPLES

Example B1

In a standard liquid dilution antimicrobial assay described below, Loloatin B was found to be selectively antimcrobial with the minimum inhibitory concentrations listed in Table 2 below. Antimicrobial activity was determined by macro-broth dilution antimicrobial susceptibility testing. A solution of Loloatin B was prepared in tryptic soy broth. Initially, a 100 μmg/ml solution of the peptide was tested. If inhibition of a target microorganism was detected, serial two-fold dilutions (in broth) of the Loloatin B solutions were tested to determine the minimal inhibitory concentration (MIC) of Loloatin B for each target organism Target organisms tested are identified in Table 2. Turbidity standardized suspensions of each organism were prepared according to accepted protocols using a 0.5 McFarland turbidity standard, and these standardized suspensions were used to inoculate a tube containing Loloatin B. Activity of Loloatin B was indicated by lack of growth (turbidity) of one or more of the target organisms.

See Woods, G. L. et al., "Antibacterial susceptibility tests: dilution and disk diffusion methods, *Manual of Clinical Microbiology* ($6^{th}$Ed.), Murray, Baron, Pfaller, Tenover and Yolken (Eds.), ASM Press, Washington D.C., 1995, pp. 1327–1341.

TABLE 2

| Minimum Inhibitory Concentrations of Loloatin B Against a Panel of Human Pathogens | |
|---|---|
| Methicillin resistant *Staphylococcus aureus* | <2 μg/mL |
| Vancomycin resistant *Enterococcus faecalis* | <2 μg/mL |
| Penicillin resistant *Streptococcus pneumoniae* | <2 μg/mL |
| *Candida albicans* | >100 μg/mL |
| *Pseudomonas aeruginosa* | >100 μg/mL |
| *Enterobacter cloacae* | >100 μg/mL |
| *Xanthomonas maltophilia* | >100 μg/mL |
| *Escherichia coli* | >100 μg/mL |

Example B2

Antimicrobial activity was determined by macrobroth dilution antimicrobial susceptibility testing. Solutions of the cyclic decapeptides (Loloatin A, B and C) and a control (vancomycin) were prepared in tryptic soy broth. Initially, a 100 μg/ml solution of each compound was tested. When inhibition of target microorganism was detected, serial two-fold dilutions of the compound in broth were tested to determine the minimal inhibitory concentration (MIC) of each compound for each target organisms. Target organisms tested are listed below in Table 3, and included methicillin resistant *Staphylococcus aureus*, vancomycin resistant Enterococcus sp. *Escherichia coli*, multiply drug resistant *Pseudomonas aeruginosa; Stenofrophomonas maltophilia* and *Candida albicans*. Turbidity standardized suspensions of each organism were prepared according to accepted protocols using a 0.5 McFarland turbidity standard, and these standardized suspensions were used to inoculate the tubes containing the compounds. Activity of a compound was indicated by lack of growth (turbidity) of one or more of the target organisms. See Woods, G. L. and Washington, J. A., "Antibacterial susceptibility tests: dilution and disk diffusion methods, *Manual of Clinical Microbiology* ($6^{th}$ Ed.), Murray, Baron, Pfaller, Tenover and Yolken Eds.), ASM Press, Washington D.C., 1995, pp. 1327–1341. Other compounds of the invention may be screened and evaluated for antibiotic activity in the same manner.

The data of Table 3 demonstrates that Loloatin C has excellent activity against *Escherichia coli*, a gram negative rod bacteria.

TABLE 3

ANTIBACTERIAL ACTIVITY OF THE LOLOATINS (BROTH DILUTION MICS IN μG/ML)

| | Loloatin A | Loloatin B | Loloatin C | Vanco-mycin |
|---|---|---|---|---|
| *S. aureus* (MRSA) | 2–4 | 2–4 | 0.5–1 | |
| *Enterococcus faecalis* (ATCC51299) | 2–4 | 2–4 | 2–4 | 20 |
| *Enterococcus faecalis* (13242) | 2–4 | 2–4 | 1–2 | >100 |
| *Enterococcus faecium* (F4641) | 2–4 | 2–4 | 2 | 6 |
| *Enterococcus faecium* (19007) | 2–4 | 2–4 | 2 | >100 |
| *Enterococcus gallinarum* | 2–4 | 2–4 | 1–2 | 6 |
| Group A Streptococcus (19615) | <0.25 | <0.25 | <0.25 | |
| Group B Streptococcus (12401) | <1 | <1 | <0.25 | |
| *Candida albicans* | 16 | 16 | 16 | |
| *Pseudomonas aeruginosa* | >100 | #100 | >100 | |
| *Enterobacter cloacae* | >100 | >100 | >100 | |
| *Stenotrophomonas maltophilia* | >100 | >100 | >100 | |
| *Escherichia coli* | >100 | >100 | 1–2 | |

All publications and patent applications mentioned in this specification are herein incorporated by reference to the same extent as if each individual publication or patent application was specifically and individually incorporated by reference.

From the foregoing, it will be evident that, although specific embodiments of the invention have been described herein for purposes of illustration, various modifications may be made without deviating from the spirit and scope of the invention.

What is claimed is:

1. An isolated compound selected from the group consisting of:

cyclo [L-Val-L-Orn-L-Leu-D-Tyr-L-Pro-L-Phe-D-Phe-L-Asn-L-Asp-L-Tyr] (SEQ ID NO:1);

cyclo [L-Val-L-Orn-L-Leu-D-Tyr-L-Pro-L-Phe-D-Phe-L-Asn-L-Asp-L-Trp] (SEQ ID NO:2); and cyclo [L-Val-L-Orn-L-Leu-D-Tyr-L-Pro-L-Trp-D-Phe-L-Asn-L-Asp-L-Trp] (SEQ ID NO:3).

2. A compound of claim 1 having the formula:

cyclo [L-Val-L-Orn-L-Leu-D-Tyr-L-Pro-L-Phe-D-Phe-L-Asn-L-Asp-L-Tyr] (SEQ ID NO:1).

3. A compound of claim 1 having the formula:

cyclo [L-Val-L-Orn-L-Leu-D-Tyr-L-Pro-L-Phe-D-Phe-L-Asn-L-Asp-L-Trp] (SEQ ID NO:2).

4. A compound of claim 1 having the formula:

cyclo [L-Val-L-Orn-L-Leu-D-Tyr-L-Pro-L-Trp-D-Phe-L-Asn-L-Asp-L-Trp] (SEQ ID NO:3).

5. A pharmaceutical composition comprising a compound of any of claims 1, 2, 3, or 4, and a pharmaceutically acceptable carrier.

6. A method for the treatment of a patient afflicted with a bacterial infection comprising the administration to said patient of a therapeutically effective amount of a compound of any of claims 1, 2, 3, or 4.

* * * * *